United States Patent
Padwal et al.

(10) Patent No.: US 11,911,220 B2
(45) Date of Patent: Feb. 27, 2024

(54) SYSTEMS AND METHODS FOR ULTRASOUND SCANNING

(71) Applicant: Verathon Inc., Bothell, WA (US)

(72) Inventors: Monali Padwal, Mercer Island, WA (US); Joon Hwan Choi, Bothell, WA (US); Nasser Saber, Kirkland, WA (US); Fuxing Yang, Bothell, WA (US)

(73) Assignee: Verathon Inc., Bothell, WA (US)

( * ) Notice: Subject to any disclaimer, the term of this patent is extended or adjusted under 35 U.S.C. 154(b) by 151 days.

(21) Appl. No.: 17/072,101

(22) Filed: Oct. 16, 2020

(65) Prior Publication Data
US 2021/0113194 A1 Apr. 22, 2021

Related U.S. Application Data
(60) Provisional application No. 62/916,423, filed on Oct. 17, 2019.

(51) Int. Cl.
*A61B 8/08* (2006.01)
*G06T 7/00* (2017.01)

(52) U.S. Cl.
CPC .......... *A61B 8/5223* (2013.01); *A61B 8/0891* (2013.01); *G06T 7/0012* (2013.01);
(Continued)

(58) Field of Classification Search
CPC ......... G06T 7/0012; G06T 2207/30101; G06T 2207/10132; A61B 8/5223; A61B 8/0891;
(Continued)

(56) References Cited

U.S. PATENT DOCUMENTS

| | | | |
|---|---|---|---|
| 6,554,771 B1 * | 4/2003 | Buil ......................... | A61B 8/00 600/443 |
| 6,905,468 B2 * | 6/2005 | McMorrow ........ | A61B 5/02007 600/443 |

(Continued)

FOREIGN PATENT DOCUMENTS

| | | |
|---|---|---|
| CA | 2 235 947 C | 1/2003 |
| EP | 0 602 949 A2 | 6/1994 |

(Continued)

OTHER PUBLICATIONS

Kleinstreuer, C., Li, Z. Analysis and computer program for rupture-risk prediction of abdominal aortic aneurysms. BioMed Eng OnLine 5, 19 (2006). https://doi.org/10.1186/1475-925X-5-19 (Year: 2006).*

(Continued)

*Primary Examiner* — Aaron W Carter
*Assistant Examiner* — Courtney Joan Nelson
(74) *Attorney, Agent, or Firm* — Snyder, Clark, Lesch & Chung, LLP

(57) ABSTRACT

A system includes a number of transducers configured to transmit ultrasound signals directed to a target blood vessel and receive echo information associated with the transmitted ultrasound signals. The system also includes a processing device configured to process the echo information, generate ultrasound images of the blood vessel at a number of locations and generate an estimated diameter of the blood vessel at the locations. The processing device is also configured to output image information associated with the blood vessel and output a maximum estimated diameter of the blood vessel or the estimated diameters at the number of locations based on the image information.

21 Claims, 22 Drawing Sheets

(52) U.S. Cl.
CPC .............. *G06T 2207/10132* (2013.01); *G06T 2207/30101* (2013.01)

(58) Field of Classification Search
CPC . A61B 8/4483; A61B 8/4494; A61B 18/1492; A61B 2090/378; A61B 8/085; A61B 2034/2063
See application file for complete search history.

(56) References Cited

U.S. PATENT DOCUMENTS

| | | | |
|---|---|---|---|
| 9,955,946 | B2 | 5/2018 | Miller et al. |
| 2004/0054280 | A1 | 3/2004 | McMorrow et al. |
| 2006/0241459 | A1* | 10/2006 | Tai ..................... G01S 15/8979 600/437 |
| 2007/0078345 | A1* | 4/2007 | Mo ........................ G10K 11/32 600/459 |
| 2008/0300489 | A1* | 12/2008 | Schutz ................. A61B 5/6826 600/459 |
| 2009/0306509 | A1* | 12/2009 | Pedersen ............. G01S 15/8936 600/446 |
| 2011/0125022 | A1 | 5/2011 | Lazebnik |
| 2012/0095343 | A1 | 4/2012 | Smith et al. |
| 2013/0331704 | A1* | 12/2013 | Salzman .............. A61B 8/5223 600/459 |
| 2013/0345566 | A1 | 12/2013 | Weitzel et al. |
| 2014/0276615 | A1 | 9/2014 | Laroya |
| 2016/0000403 | A1 | 1/2016 | Vilkomerson |
| 2016/0199029 | A1 | 7/2016 | Struijk et al. |
| 2017/0124701 | A1 | 5/2017 | Liang et al. |
| 2018/0064421 | A1 | 3/2018 | Moshavegh et al. |
| 2018/0242945 | A1 | 8/2018 | Tomoeda |

FOREIGN PATENT DOCUMENTS

| | | | | |
|---|---|---|---|---|
| EP | 2 168 495 | B1 | 3/2012 | |
| JP | 2004-329608 | A | 11/2004 | |
| JP | 2011056291 | A | 3/2011 | |
| JP | 2011110432 | A | 6/2011 | |
| JP | WO2017/043536 | A1 | 3/2017 | |
| JP | 2018533385 | A | 11/2018 | |
| WO | WO-2007057826 | A1 * | 5/2007 | ........... A61B 5/6843 |
| WO | 2007087522 | A2 | 8/2007 | |
| WO | WO-2010017508 | A1 * | 2/2010 | ......... A61B 5/02014 |
| WO | WO-2018054969 | A1 * | 3/2018 | ........... A61B 8/0841 |
| WO | WO2018/065720 | A | 4/2018 | |
| WO | WO2019164662 | A1 | 8/2019 | |

OTHER PUBLICATIONS

L. Rouet, R. Ardon, J. Rouet, B. Mory, C. Dufour and A. Long, "Semi-automatic abdominal aortic aneurysms geometry assessment based on 3D ultrasound," 2010 IEEE International Ultrasonics Symposium, 2010, pp. 201-204, doi: 10.1109/ULTSYM.2010.5935590. (Year: 2010).*

Leotta, Daniel F. et al., "Measurement of abdominal aortic aneurysms with three-dimensional ultrasound imaging: Preliminary report," Journal of Vascular Surgery, vol. 33, No. 4, Apr. 1, 2001, 8 pages.

International Search Report issued in corresponding PCT Application No. PCT/US2020/055886 dated Jan. 27, 2021, 11 pages.

* cited by examiner

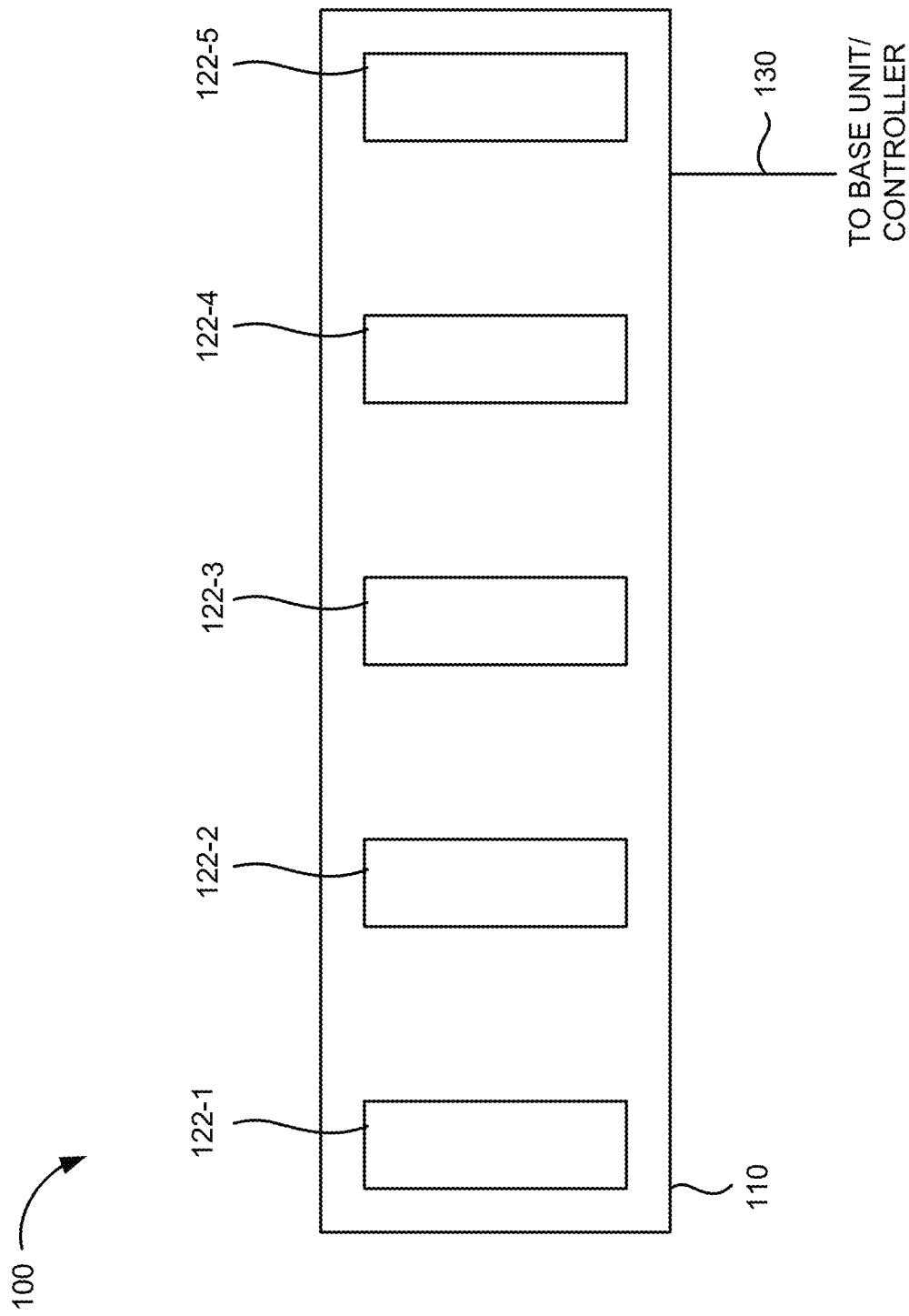

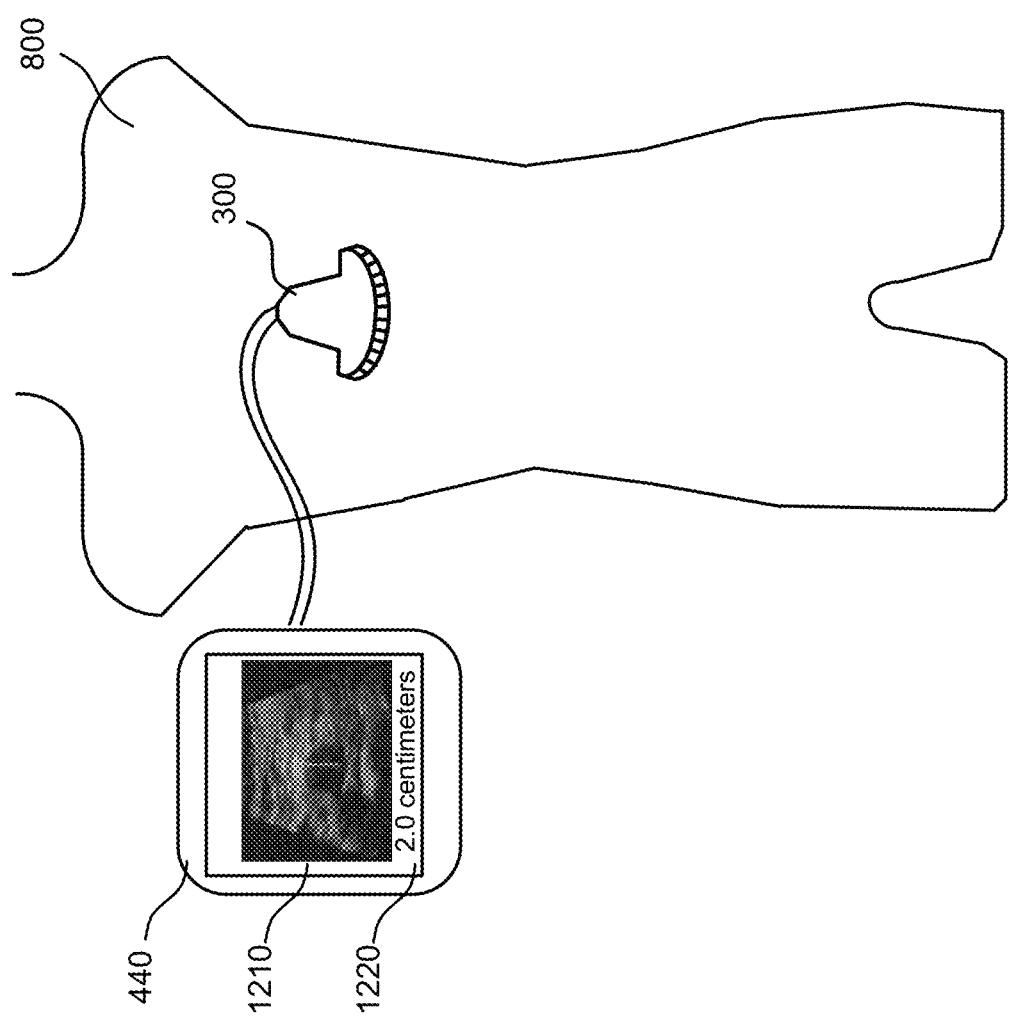

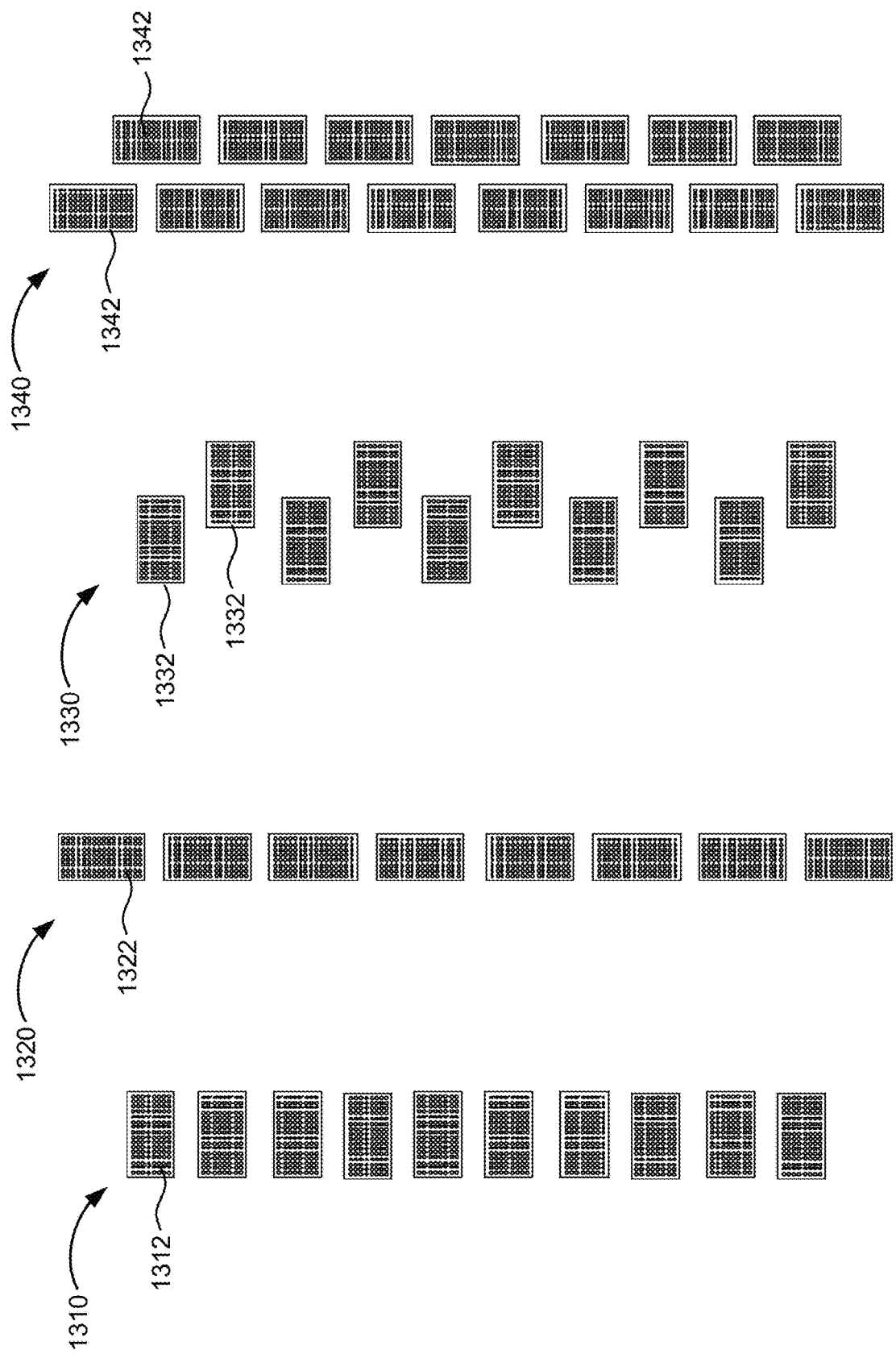

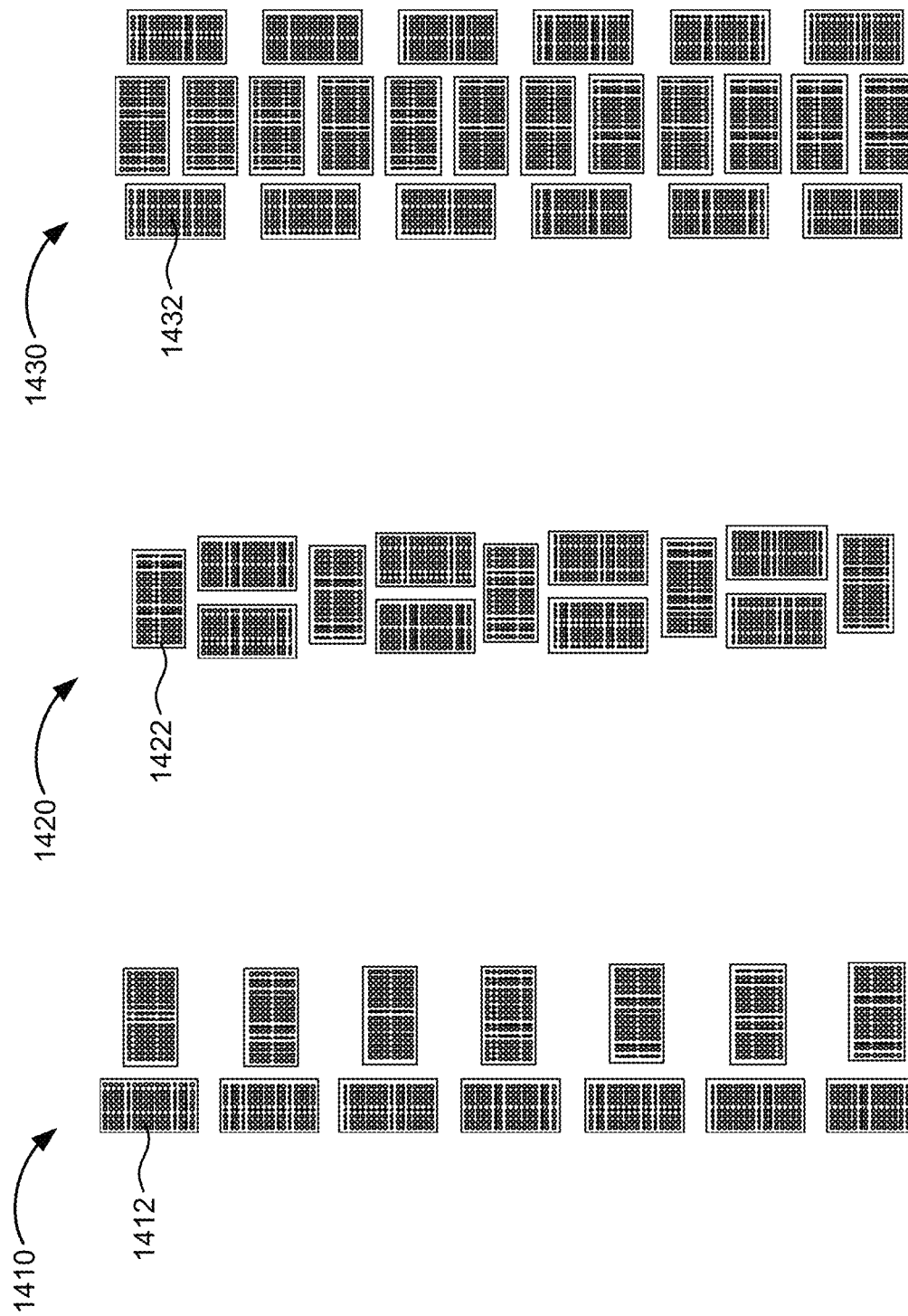

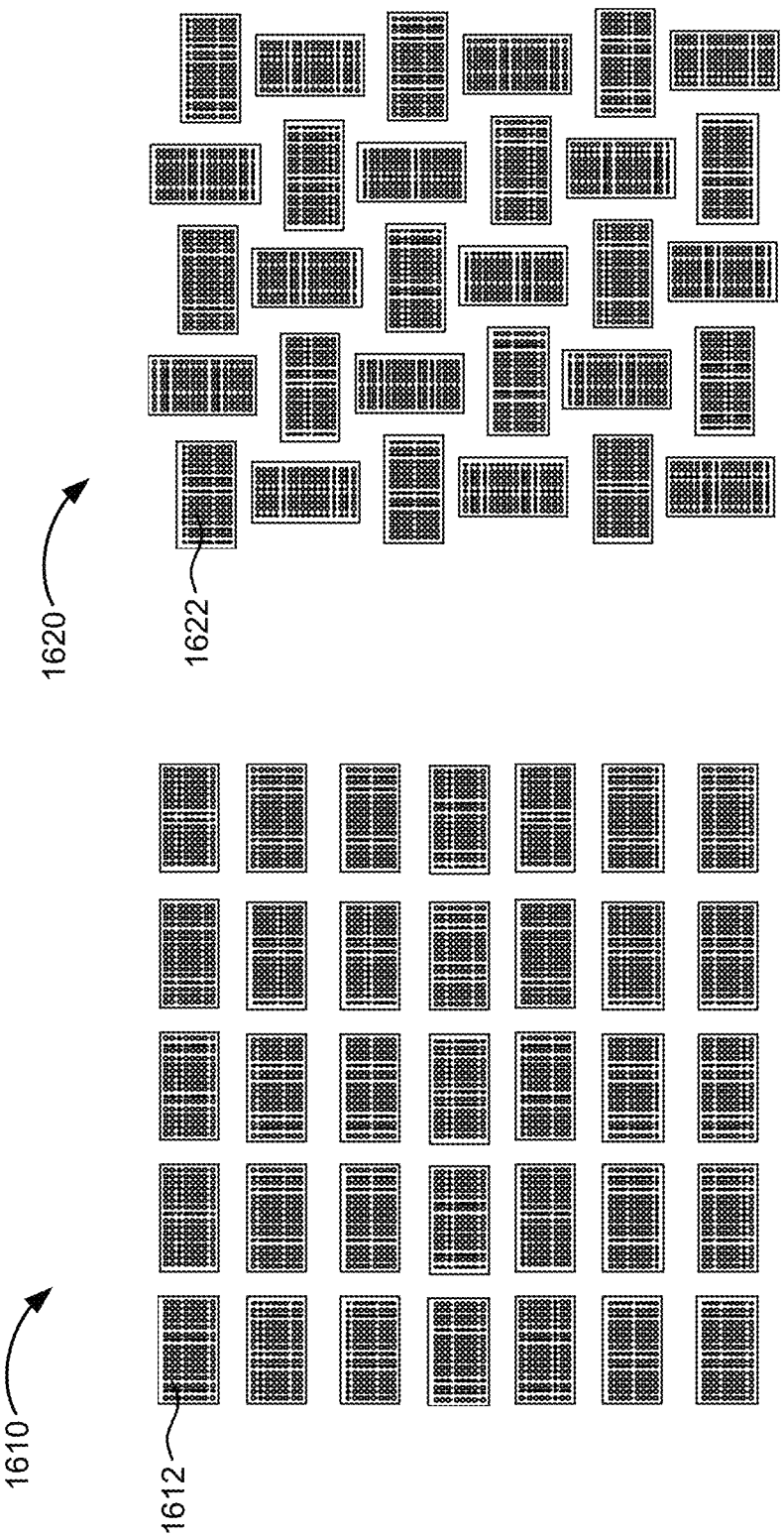

SYSTEMS AND METHODS FOR ULTRASOUND SCANNING

RELATED APPLICATION

This application claims priority under 35 U.S.C. § 119 based on U.S. Provisional Application No. 62/916,423 filed Oct. 17, 2019, the contents of which are hereby incorporated herein by reference in their entirety.

BACKGROUND INFORMATION

An abdominal aortic aneurysm (AAA) refers to a dilatation of the aorta, usually located between the diaphragm and the aortic bifurcation. Monitoring the abdominal aorta for an AAA is typically accomplished via a computed tomography (CT) scan or magnetic resonance imaging (MRI). However, imaging modalities such as CT scans, which use radiation, and MRIs are often time consuming procedures that are costly to administer.

In other situations, ultrasound scanners may be used to measure features associated with the abdominal aorta. However, monitoring features of the abdominal aorta via ultrasound is difficult due to, among other things, the low image quality associated with ultrasound imaging. In addition, current ultrasound examination of AAAs requires making antero-posterior measurements derived from a single two-dimensional image. Medical personnel analyzing such ultrasound images will often create errors associated with measuring an AAA based on an incorrect orientation of the image plane, resulting in an inaccurate measurement of the AAA. Still further, when using conventional ultrasound scanners, it is difficult for the operator to capture images of the entire abdominal aorta for analysis, unless the operator is highly skilled. As a result, analysis of the abdominal aorta is often incomplete.

BRIEF DESCRIPTION OF THE DRAWINGS

FIG. 1A is a top view of an ultrasound transducer system in accordance with an exemplary implementation;

FIG. 12 illustrates use of another ultrasonic probe on a patient in accordance with another exemplary implementation;

FIGS. 13A-13D are top views of other ultrasound transducer systems configured in linear patterns in accordance with other exemplary implementations;

FIGS. 14A-14C are top views of other ultrasound transducer systems in accordance with other exemplary implementations;

FIGS. 16A-16D are top views of other ultrasound transducer systems configured in a multi-dimensional patterns in accordance with other exemplary implementations;

DETAILED DESCRIPTION OF PREFERRED EMBODIMENTS

Figure 1B:
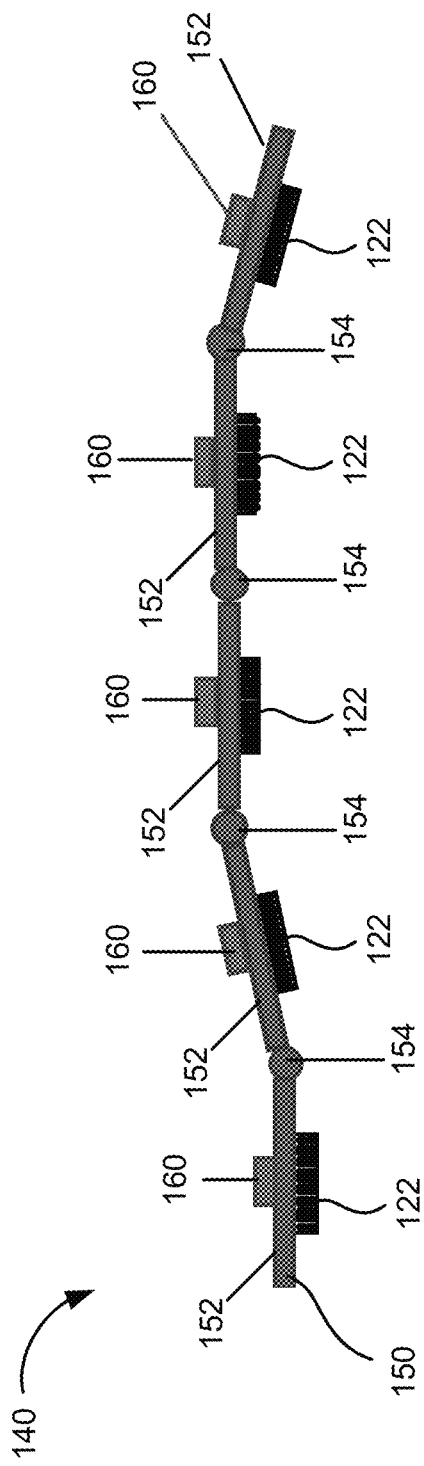
FIG. 1B is a side view of another ultrasound transducer system in accordance with another exemplary implementation.

The following detailed description refers to the accompanying drawings. The same reference numbers in different drawings may identify the same or similar elements. Also, the following detailed description does not limit the invention.

Implementations described herein relate to using ultrasound imaging for identifying an abdominal aorta and the possible existence of an abdominal aortic aneurysm (AAA). In accordance with one exemplary implementation, ultrasound imaging of the abdominal aorta may be performed using an array of capacitive micro-machined ultrasonic transducers (CMUTs) that provide images of the abdominal aorta. In another implementation, the ultrasound imaging may be performed using a curvilinear array of piezoelectric transducer elements or an array of piezoelectric micro-machined ultrasonic transducers (PMUTs). In each case, the ultrasonic imaging may provide images of the entire abdominal aorta and identify an AAA, if one exists. Implementations described herein may also automatically measure the diameter and/or other parameters of the abdominal aorta, which may provide information indicating whether an AAA exists.

In some implementations, position sensors or encoders associated with the ultrasound transducers (e.g., CMUT transducers) may be used to aid in combining various two-dimensional images generated by individual CMUT transducers. The position sensors and encoders may help provide a more accurate representation of the entire abdominal aorta and more accurate measurements associated with the abdominal aorta. Still further, machine learning, including using neural networks and deep learning, may also be used to aid in identifying and/or measuring the abdominal aorta, or other vessel, organ or structure of interest in a patient based on information obtained via the ultrasound scan.

FIG. 1A is a top view of an exemplary CMUT strip transducer system 100 (also referred to herein as CMUT system 100) that may be used to identify and measure an AAA in accordance with an exemplary implementation. Referring to FIG. 1A, CMUT system 100 includes housing 110, CMUTs 122-1 through 122-5 (referred to individually as CMUT 122, 122-X or transducer 122, or collectively as CMUTs 122 or transducers 122), and cable/connector 130. CMUT system 100 may also include additional elements, such as control-related electronics (not shown) that aid in controlling CMUT system 100, such as providing power or activating transducers 122.

In one implementation, housing 110 may be a rigid or semi-rigid housing that supports/houses CMUTs 122 along with electronics/circuitry (not shown) associated with controlling activation of transducers 122. In other implementations, housing 110 may be a flexible belt or strip that supports CMUTs 122 and the electronics. Housing 110 may be placed on a patient's abdomen area and optionally taped onto the patient's abdomen to ensure that housing 110 contacts the patient's abdomen along the entire length of housing 110. CMUTs 122 may be powered to generate ultrasonic images, as described in more detail below. In an exemplary implementation, housing 110 may also include position sensors (not shown in FIG. 1A) that aid in combining images from CMUTs 122.

Each CMUT 122 may include one or more cells, such as an array of small capacitor cells which may be connected in parallel. For example, each cell of CMUT 122 may include a top electrode which may be flexible and a fixed bottom electrode. A small gap is formed between the top electrode and the bottom electrode to form a capacitor. During operation, a voltage may be applied to the top electrode causing CMUT 122 to generate an ultrasound signal that may be used to generate imaging information for a target of interest, such as the abdominal aorta, as described in more detail below.

In CMUT system 100, CMUTs 122 are configured in a one-dimensional pattern with each CMUT 122 oriented parallel to and separated from an adjacent CMUT 122. In this manner, CMUTs 122 together obtain a field of view that captures the entire abdominal aorta. That is, based on the length of the target of interest (e.g., the abdominal aorta in this case), the number of CMUTs 122 and the separation between adjacent CMUTs 122 is designed such that ultrasonic signals generated by CMUTs 122 are transmitted to reach the entire length of the abdominal aorta. As a result, the overall length of housing 110 and the number of CMUTs 122 may be based on the height of a patient. For example, for a scan of an adult, CMUT system 100 may include a longer housing 110 that includes more CMUTs 122, than a CMUT system 100 used for a child. In addition, the field of view of one CMUT 122 may overlap with the field of view of an adjacent CMUT 122. The images from CMUTs 122 may then be combined to provide a complete view of the target of interest, such as the abdominal aorta, as described in more detail below.

Connector/cable 130 may be coupled on one end to a base unit/controller that is used by medical personnel to initiate an ultrasound scan using CMUT system 100 and coupled on the other end to CMUT system 100. In one implementation, the base unit/controller provides both control signals and power to activate CMUTs 122. For example, a voltage may be supplied to CMUTs 122 from the controller via cable 130 in response to initiation of an ultrasound scan, as described in detail below.

FIG. 1B illustrates a side view of another exemplary CMUT strip transducer system 140 that includes CMUTs 122. In this implementation, CMUT strip transducer system 140 (also referred to as CMUT system 140) includes a semi-rigid or flexible housing 150. Housing 150 may be made up of a number of sections or portions 152 connected to one another via elements/structures 154 that, in the example of FIG. 1B, have a circular cross-sectional shape. Elements 154 may extend the width of housing 150 and allow each section 152 to be angularly offset with respect to the adjacent section 152. Elements 154 may act as pivot points or hinges to allow housing 150 to adhere to contours of the human body, such as contours of the abdomen. That is, each section 152 of CMUT system 140 may contact a portion of the patient's abdomen such that CMUT system 140 follows the contour of the patient's abdomen/midsection. This may allow transducers 122 to maintain contact with the patient's skin and obtain high quality images along the entire length of the target of interest, such as the abdominal aorta. In some implementations, each of CMUTs 122 may be individually adjusted to ensure a good contact with the curved skin surface to reduce artifacts in the ultrasound imaging, such as bowel gas shadows.

CMUT system 140 may also include position sensors 160. Position sensors 160 may allow the base unit/controller to "register" images by rotating the images from transducers 122 based on position information from position sensors 160 from transducers 122 (e.g., based on the position of the respective transducers 122). For example, CMUTs 122 may generate imaging planes with overlapping fields of view, or non-overlapping fields of view. Each position sensor 160 may generate location or position information with respect to a reference point, such as the end or side of housing 150, an adjacent transducer 122, an adjacent position encoder 160, etc. In an exemplary implementation, position sensors 160 may be microelectromechanical (MEMS) position sensors, such as gyroscopes and/or accelerometers that provide position information, including angular information with respect to the images generated by transducers 122 that may be angularly offset from one another. Based on the position information, the base unit/controller may register and then combine images, such as B-mode images generated by CMUTs 122, to generate an accurate image of the entire target of interest, as described in more detail below. For example, the base unit/controller can register multiple B-mode images by properly rotating the images based on the position information. In some configurations in which multiple B-mode images associated with different CMUTs overlap with each other, the overlapping images may be stitched together or combined after registration, as described in more detail below. In situations in which the images do no not overlap, the images may also be used to generate views of the entire abdominal aorta, as described in detail below.

Figure 1C:
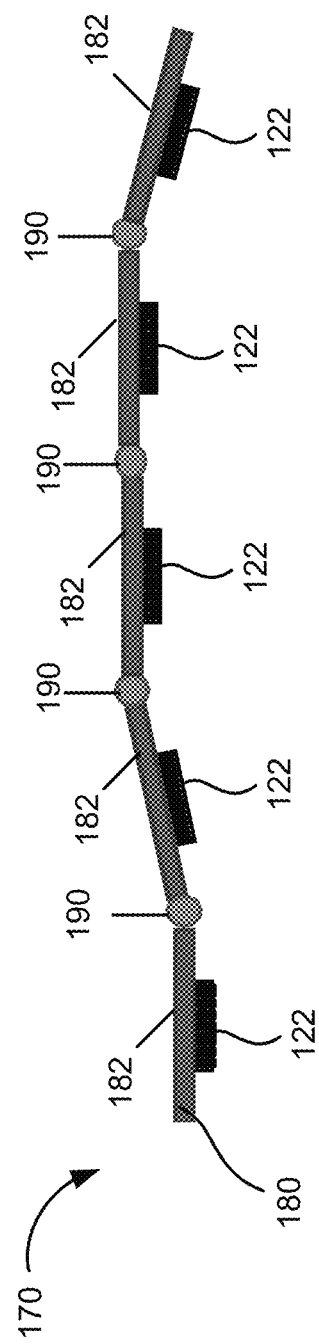
FIG. 1C is a side view of another ultrasound transducer system in accordance with another exemplary implementation.

FIG. 1C illustrates a side view of another exemplary CMUT strip transducer system 170 that includes CMUTs 122. In this implementation, CMUT strip transducer system 170 (also referred to herein as CMUT system 170) includes a semi-rigid or flexible housing 180 similar to housing 150 described above with respect to FIG. 1B. That is, housing 180 may be made up of a number of sections or portions 182 connected to one another via elements 190 that have a circular cross-sectional shape and extend the width of housing 180. Elements 190 may allow each section 182 to be angularly offset with respect to the adjacent section 182 and allow each section 182 to contact a portion of the patient's abdomen.

Figure 1D:
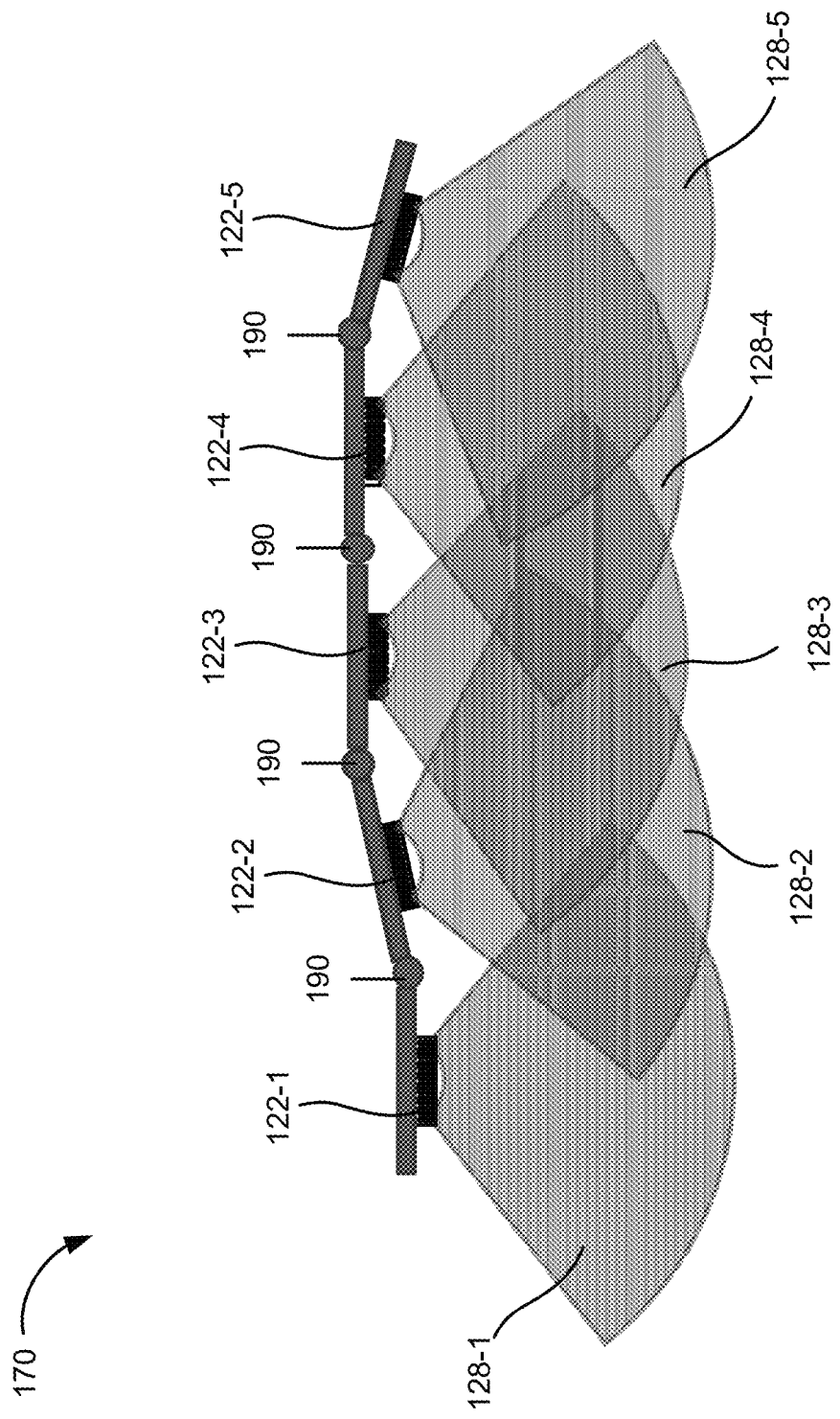
FIG. 1D is a side view of the transducer system of FIG. 1C illustrating fields of view associated with the transducers.

In this implementation, elements 190 may also include position encoders that provide position information associated with images from transducers 122 to allow a base unit/controller to register and/or combine various images from transducers 122 based on the position of the respective transducers 122 provided by position encoders 190. For example, in one implementation, CMUTs 122 may generate imaging planes with overlapping fields of view, as illustrated in FIG. 1D. Referring to FIG. 1D, CMUTs 122-1 through 122-5 may provide ultrasound signals with fields of view 128-1 through 128-5, respectively, which overlap with the adjacent fields of view. Based on information from position encoders 190, a base unit/controller may combine ultrasonic images (e.g., B-mode images) including the overlapping fields of view 128-1 through 128-5 to generate an accurate image of the target of interest along the entire length of the target of interest (e.g., the abdominal aorta), as described in more detail below. In other implementations, the fields of view associated with CMUTs 122 may not overlap with each other.

Figure 2:
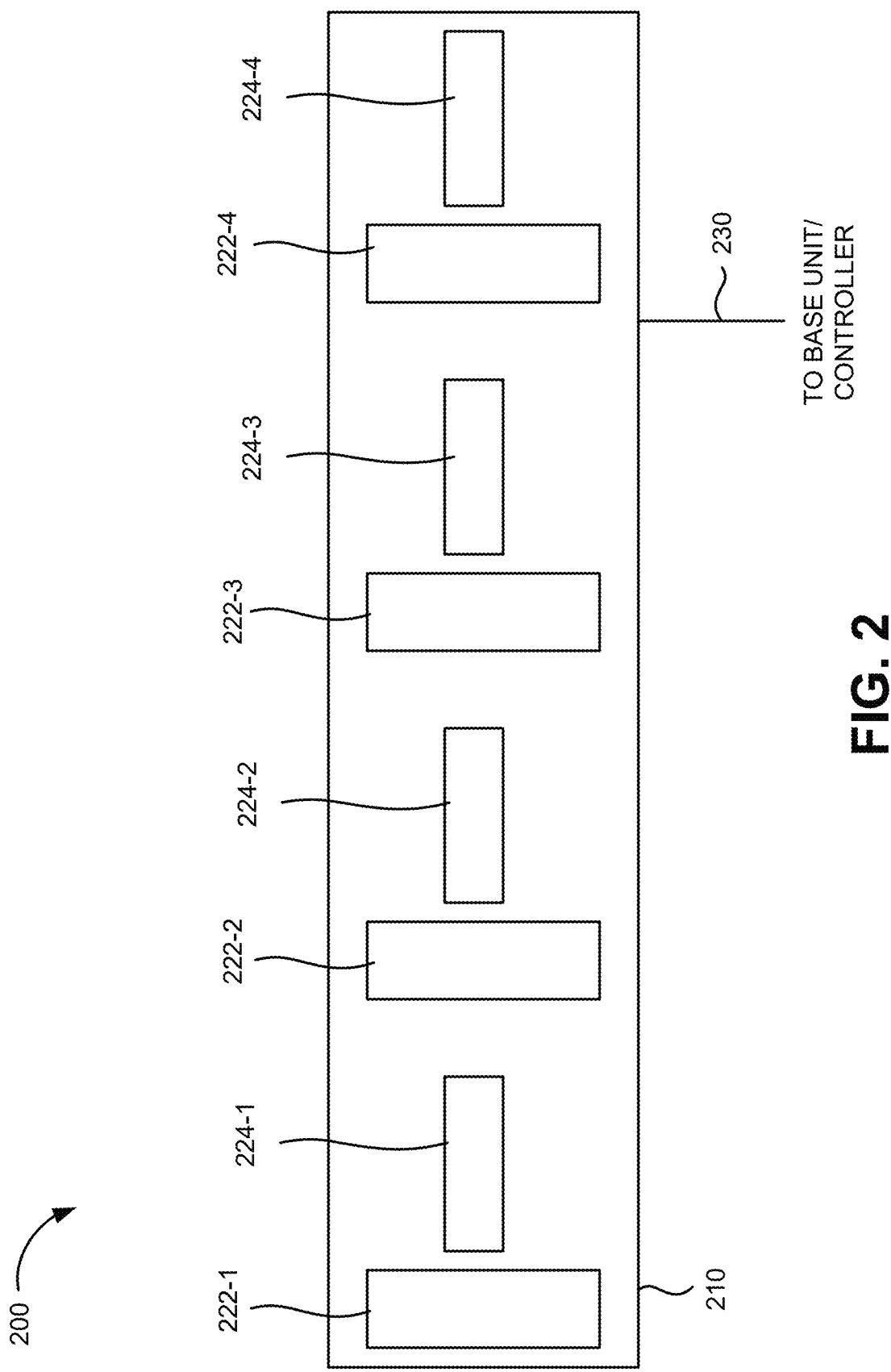
FIG. 2 is a top view of another ultrasound transducer system in accordance with another exemplary implementation.

FIG. 2 is a top view of another exemplary CMUT strip transducer system 200 that may be used to image and measure an abdominal aorta in accordance with an exemplary implementation. Referring to FIG. 2, CMUT strip transducer system 200 (also referred to as CMUT system 200) includes housing 210, CMUTs 222-1 through 222-4 (referred to individually as CMUT 222, 222-X or transducer 222, or collectively as CMUTs 222 or transducers 222) and CMUTs 224-1 through 224-4 (referred to individually as CMUTs 224, 224-X or transducers 224, or collectively as CMUTs 224 or transducers 224). In this implementation, CMUTs 222 and 224 may be arranged in pairs, with each CMUT 222 oriented in a first direction and each CMUT 224 oriented perpendicularly to the adjacent CMUT 222. In this implementations, CMUTs 222 and 224 together may provide biplane imaging in which both sagittal and transverse views may be provided by each CMUT pair 222 and 224 at each location in CMUT system 200. In addition, the orientation of transducers 224 perpendicular to transducers 222 provides a field of view that extends orthogonally with respect to the fields of view illustrated in FIG. 1D. In this implementation, relatively inexperienced medical personnel may be able to use CMUT system 200 to completely capture the abdominal aorta due to, among other things, the sagittal and transverse fields of view provided by CMUT system 200.

In one implementation, housing 210 may be a rigid, semi-rigid or flexible housing that supports/houses CMUTs 222 and 224 along with electronics/circuitry (not shown) associated with controlling activation of transducers 222 and 224. Housing 210 may be placed on a patient's abdomen area and optionally taped or otherwise adhered to the patient's abdomen area. CMUTs 222 and 224 may be powered to generate ultrasonic images, as described in more detail below. In an exemplary implementation housing 110 may also include position sensors (not shown in FIG. 2) similar to those described above with respect to FIGS. 1B and 1C (e.g., position sensors/encoders 160 and 190) that aid in registering and rotating images based on position information and/or combining images from CMUTs 222 and 224. In addition, CMUT system 200 may include portions that are angularly offset with respect to other portions similar to those described above with respect to FIGS. 1B and 1C to conform to the contours of the patient's body.

Each CMUT 222 and 224 may be similar to CMUTs 122 described above. That is, each CMUT 222 and 224 may include one or more cells with each cell including top and bottom electrodes separated by a gap to form a capacitor. During operation, a voltage may be applied to the top electrode and transducers 222 and 224 generate ultrasound signals that may be used to generate imaging information for a target of interest, such as the abdominal aorta, as described in more detail below.

Connector/cable 230 may be similar to cable 130 described above. For example, a voltage and control signals may be supplied from a base unit/controller to transducers 222 and 224 via cable 230 to activate transducers 222 and 224 and generate ultrasound signals.

Figure 3:
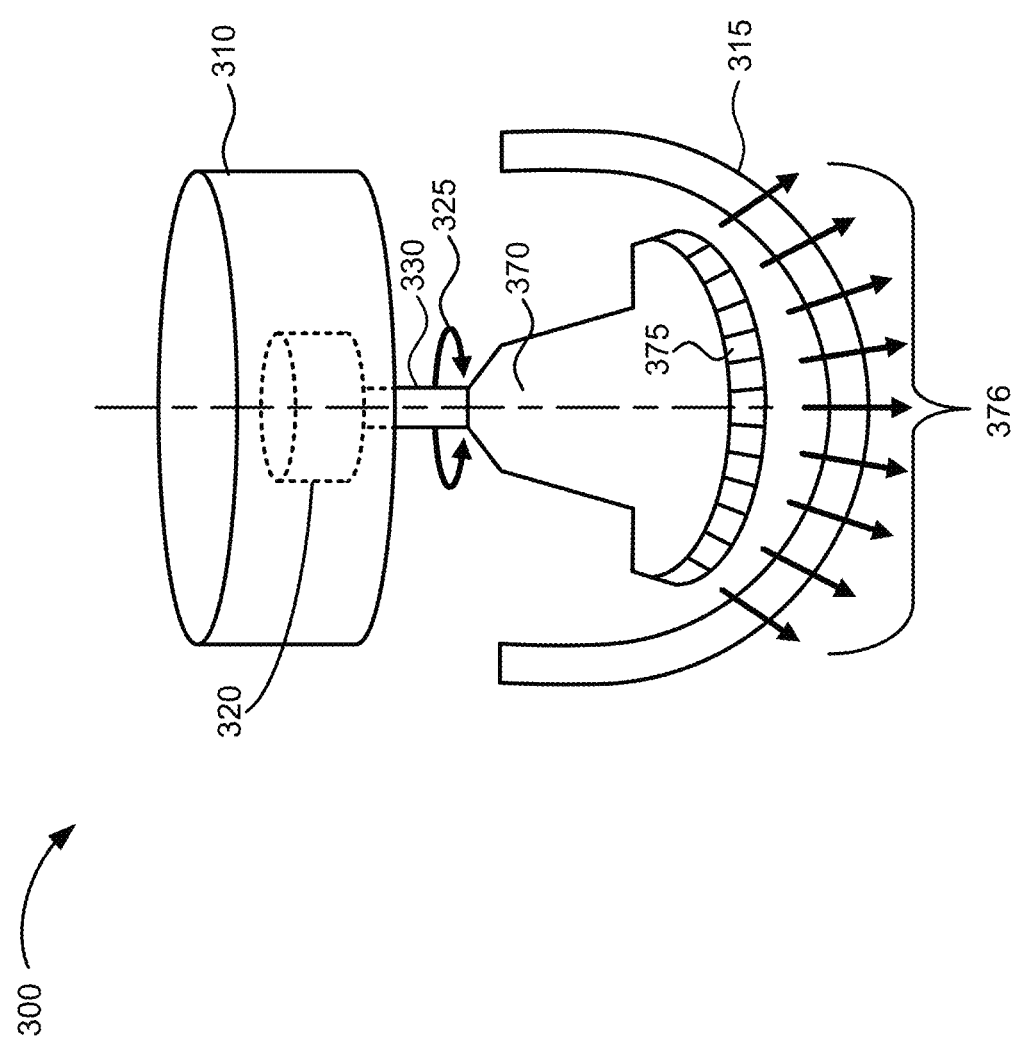
FIG. 3 illustrates a curvilinear ultrasound probe in accordance with another exemplary implementation.

FIG. 3 is a diagram of an ultrasound probe 300 that may be used in accordance with another exemplary implementation described herein. For example, ultrasound probe 300 may be used to scan a target of interest, such as an abdominal aorta. Referring to FIG. 3, ultrasound probe 300 may include a one-dimensional (1D) array of transducer elements coupled to a rotation motor. In this implementation, ultrasound probe 300 may include a base 310 connected to dome 315, a theta motor 320 (also referred to as a rotational motor 320), a spindle 330, and a transducer bucket 370 with a 1D transducer array 375. Theta motor 320 and/or 1D transducer array 375 may include wired or wireless electrical connections that electrically connect theta motor 320 and/or 1D transducer array 375 to a base unit/controller unit (not shown in FIG. 3).

Base 310 may house theta motor 320 and provide structural support to ultrasound probe 300. Base 310 may connect to dome 315 and may form a seal with dome 315 to protect the components of ultrasound probe 300 from the external environment. Theta motor 320 may rotate spindle 330 with respect to base 310 in a longitudinal direction with respect to 1D transducer array 375 by rotating around theta rotational plane 325. Spindle 330 may terminate in transducer bucket 370. 1D transducer array 375 may be mounted to transducer bucket 370. 1D transducer array 375 may include a curved 1D array of piezoelectric transducers, capacitive transducers, and/or other types of ultrasound transducers. Alternatively, 1D transducer array 375 may include a linear array or phased array of piezoelectric transducers. 1D transducer array 375 may convert electrical signals to ultrasound signals at a particular ultrasound frequency or range of ultrasound frequencies, may receive reflected ultrasound signals (e.g., echoes, etc.), and may convert the received ultrasound signals to electrical signals. In an exemplary implementation, probe 300 transmits ultrasound signals in a range that extends from approximately two megahertz (MHz) to approximately 10 or more MHz (e.g., 18 MHz). Each element of 1D transducer array 375 may transmit and receive ultrasound signals in a particular direction of a set of directions, illustrated as 376 in FIG. 3. Thus, together, the elements of 1D transducer array 375 may generate ultrasound image data for a particular plane. In a three-dimensional (3D) scan mode, theta motor 320 may cycle through a set of planes one or more times to obtain a full 3D scan of an area of interest. In each particular plane of the set of planes, 1D transducer array 375 may obtain ultrasound image data for the particular plane.

In some implementations, ultrasound probe 300 may not include base 310, theta motor 320 and/or dome 315. For example, ultrasound probe 300 may correspond to a handheld probe that is moved manually by a user to different positions, such as positions over the abdomen of a patient to obtain images of the abdominal aorta, as described in detail below.

Figure 4:
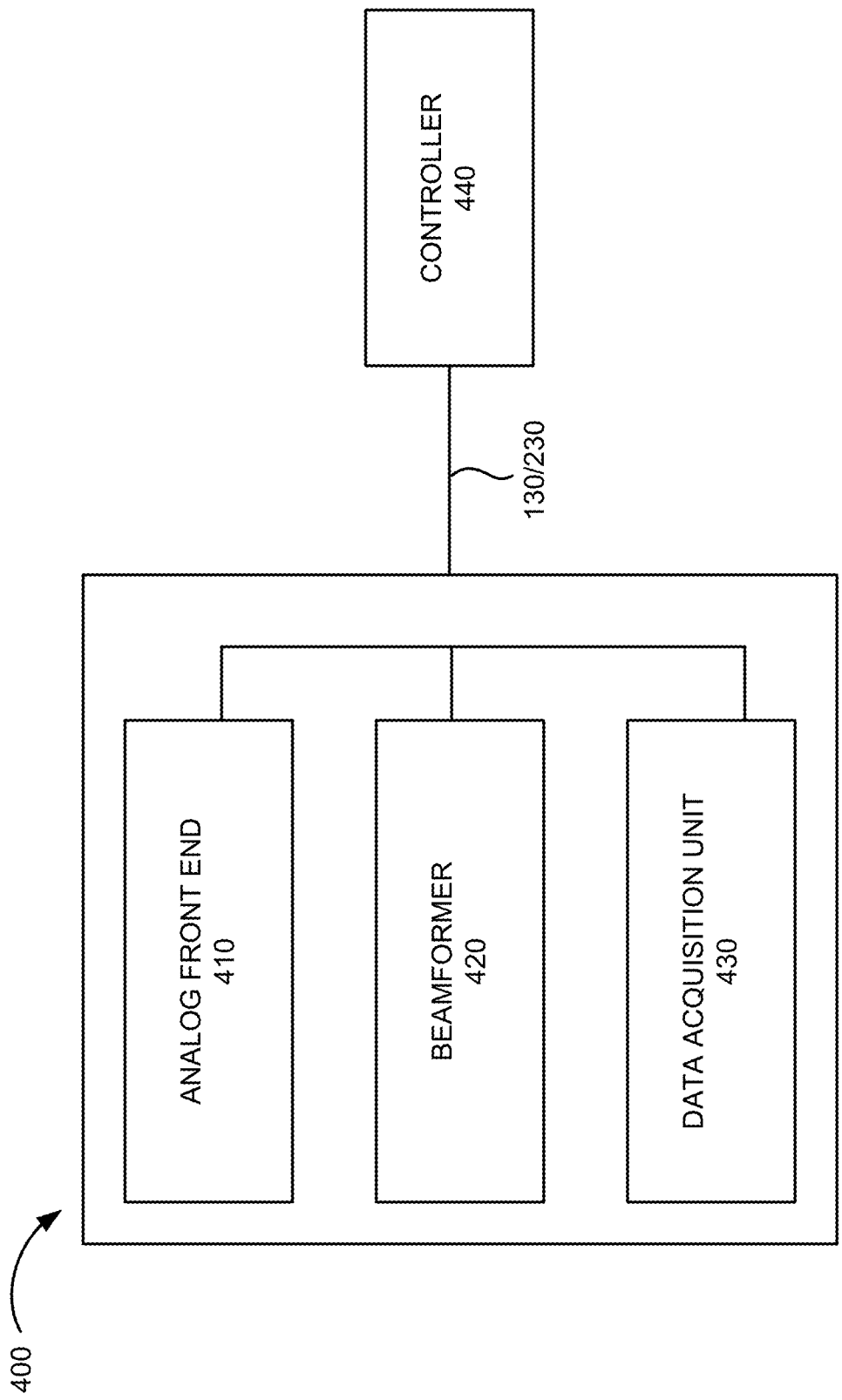
FIG. 4 illustrates an exemplary configuration of logic elements included in the ultrasound transducer systems of FIGS. 1A-1C, FIG. 2 and/or FIG. 3.

FIG. 4 is a block diagram of functional logic components 400 implemented in CMUT strip transducer systems 100, 140, 170 and/or 200 and/or probe 300 in accordance with an exemplary implementation. For example, for CMUT systems 100, 140, 170 and/or 200, components 400 may be implemented within housings 110, 150, 180 and 210, respectively. For probe 300, components 400 may be implemented within transducer bucket 370, dome 315 or in another portion of probe 300. Referring to FIG. 4, components 400 include an analog front end 410, beamformer 420 and data acquisition unit 430, which are coupled to controller 440.

AFE 410 may include transmit and receive signal control logic to operate the respective transducers 122, 222, 224 and/or 375. In an exemplary implementation, AFE 410 may receive control signals from controller 440. Controller 440 may be included within a base unit located externally with respect to CMUT systems 100/140/170/200 and/or probe 300 and may be operated by medical personnel to initiate a scan of a target of interest, such as the abdominal aorta, as described in more detail below.

AFE 410 may also include control logic that receives input from controller 440 via cable 130/230 and signals beamformer 420 to initiate an ultrasonic scan. For example, controller 440 may include one or more input buttons, a graphical user interface (GUI) with inputs, etc., to allow medical personnel to initiate a scan, such as an abdominal aorta scan. Controller 440 may also provide power to AFE 410 and/or beamformer 420 via cable 130/230. AFE 410 receives the input to initiate the scan and signals beamformer 420 to power CMUTs 122, 222 and/or 224 to generate ultrasound signals.

For example, AFE 410 may sequentially or simultaneously provide power to CMUTs 122-1 through 122-5 described above with respect to FIG. 1A-1C and sequentially or simultaneously provide power to CMUTs 222-1 through 222-4 and CMUTs 224-1 through 224-4 described above with respect to FIG. 2. In response, beamformer 420, which includes transducers 122, 222 and/or 224 generates ultrasound signals that are transmitted to the abdominal aorta. The transmitted ultrasound signals echo back from the abdominal aorta. In an exemplary implementation, the ultrasonic signals generated by beamformer 420 (e.g., CMUTs 122, 222 and 224) may have a frequency band centered at 3.0 Megahertz (MHz). It should be understood, however, that beamformer 420 may generate ultrasonic signals having other frequencies/frequency bands based on the particular application.

Data acquisition unit 430 receives the echo signals and may process the echo signals to generate image data, such as B-mode images of the abdominal aorta. Alternatively, data acquisition unit 430 may include a transmitter to transmit or forward the received echo signals for processing by controller 440, which will generate the ultrasound images of the abdominal aorta, as described in more detail below. In accordance with exemplary implementations, imaging performed by data acquisition unit 430 and/or controller 440 may use echo signals associated with the fundamental frequency of the transmitted ultrasound signals and/or echo signals associated with harmonics of the fundamental frequency. In addition, CMUT systems 100, 140, 170 and/or 200 may use pulsed wave doppler and/or color doppler in exemplary implementations to generate ultrasonic images. In each case, echo signals from the transducers 122, 222, 224 and/or 375 may be used to generate images of the entire abdominal aorta.

The exemplary configuration illustrated in FIG. 4 is provided for simplicity. Components 400 may include more or fewer logic units/devices than illustrated in FIG. 4. For example, components 400 may include additional elements, such as communication interfaces (e.g., radio frequency transceivers) that transmit and receive information via external networks to aid in analyzing ultrasound signals to identify a target in a region of interest.

Figure 5:
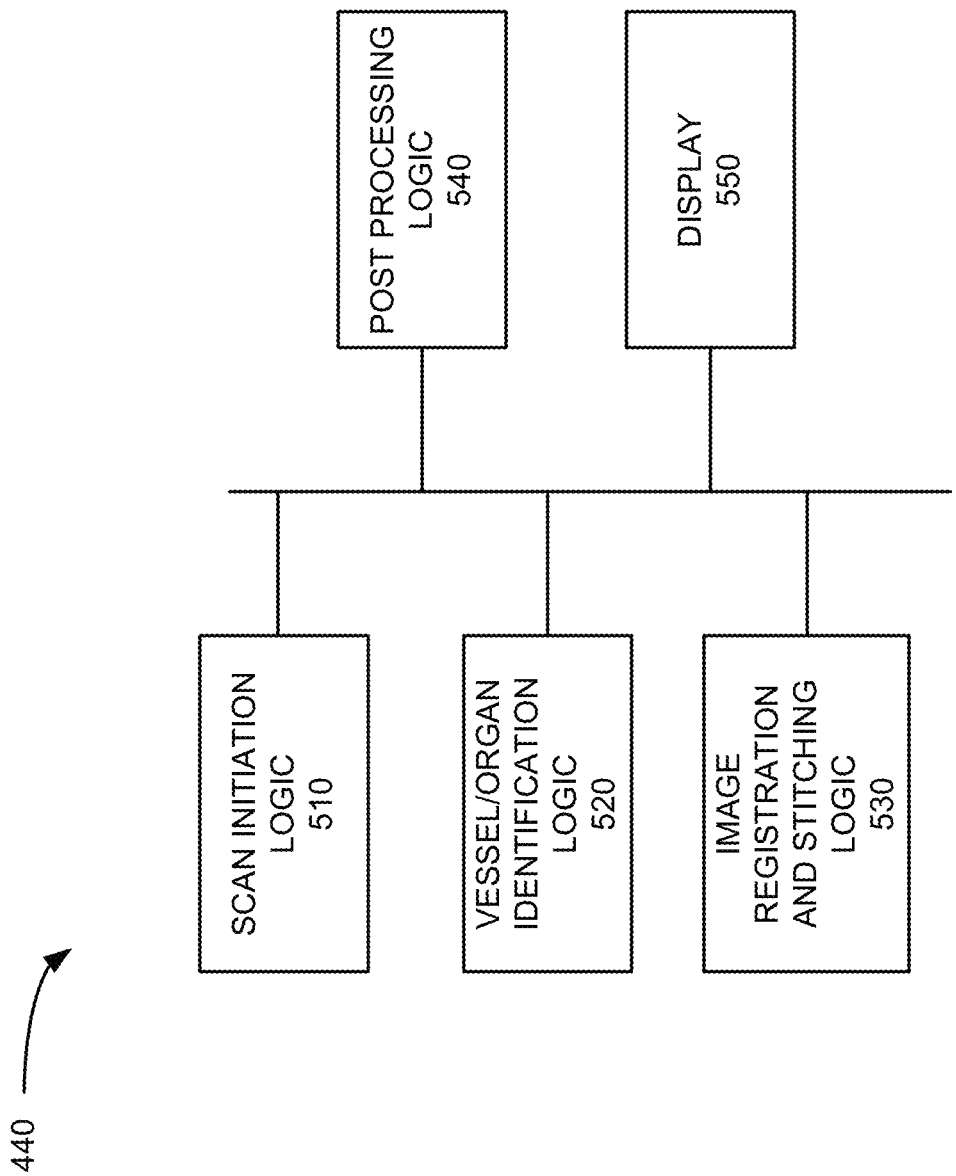
FIG. 5 illustrates an exemplary configuration of logic elements included in a base unit or controller in accordance with an exemplary implementation.

FIG. 5 is a block diagram of functional logic components implemented in controller 440 in accordance with an exemplary implementation. Referring to FIG. 5, controller 440 includes scan initiation logic 510, vessel/organ identification logic 520, image registration and stitching logic 530, post-processing logic 540 and display 550. As described above, in an exemplary implementation, controller 440 may be located externally with respect to CMUT systems 110, 140, 170 and 200 and/or probe 300 used to generate the ultrasonic signals. In some implementations, controller 440 may couple to CMUT systems 100/140/170/200 and/or probe 300 via a wireless connection to the Internet or to a local area network within a hospital, doctor's office, etc. For example, CMUT system 100/140/170/200 may transmit echo data and/or image data to controller 440 via, for example, a wireless connection (e.g., WiFi or some other wireless protocol/technology).

As described above, CMUT systems 100, 140, 170 and 200 may include one or more CMUTs that produce ultrasound signals and data acquisition unit 430 may include one or more receivers that receive echoes from the transmitted signals. In an exemplary implementation, data acquisition unit 430 obtains echo data (e.g., at the fundamental frequency and/or harmonics of the fundamental frequency) associated with multiple scan planes corresponding to the region of interest in a patient, such as regions including the abdominal aorta. Data acquisition unit 430 may receive the echo data and transmit the echo data to controller 440. Controller 440 may use the echo data to generate two-dimensional (2D) B-mode image data to identify the abdominal aorta and/or the size of an AAA located in the abdominal aorta. In other implementations, data acquisition unit 430 may receive echo data that is processed to generate three-dimensional (3D) image data that can be used to determine the size of an AAA within the abdominal aorta.

Scan initiation logic 510 may include one or more input buttons, a graphical user interface (GUI), etc., with selections to initiate various types of scans, such as an abdominal aorta scan. Scan initiation logic 510 may also include logic to receive the scan input selection from a user (e.g., medical personnel), identify the input and initiate the scan.

Vessel/organ identification logic 520 may process the echo data received in response to the transmitted ultrasound signals to generate images associated with the scan. For example, vessel/organ identification logic 520 may detect the aorta based on, for example, differentiation of pixel intensity (e.g., echo data received by data acquisition unit 430). As an example of vessel identification, in a 2D image, a blood carrying vessel may be identified as a dark region within an area of lighter-shaded pixels, where the lighter-shaded pixels typically represent body tissues. In some implementations, vessel/organ identification logic 520 may also apply noise reduction of the raw B-mode image data received from data acquisition unit 430.

Image registration and stitching logic 530 may include logic to receive data from data acquisition unit 430 and/or vessel/organ identification logic 520 and register B-mode images by rotating the images based on the position information obtained by position sensors 160 and/or position encoders 190. Image registration and stitching logic 530 may also combine various images associated with transducers 122, 222 and/or 224, such as when fields of view from the respective transducers overlap. For example, based on the location of the particular transducers 122 within housings 140 and 170, the received echo information may be combined by using the corresponding position or location information associated with the transducers 122 generating the ultrasound signals. That is, images from a top portion of the abdominal aorta near the chest area may be combined with images from the upper abdominal area to stitch together or create images of the entire abdominal aorta. For example, image registration and stitching logic 530 may provide a reconstruction function to generate an image of the entire abdominal aorta by combining all segments associated with abdominal aorta.

Post processing logic 540 may include logic to identify vessel walls, such as the walls of an abdominal aorta, the existence of AAA, etc. Post processing logic 540 may also provide "smoothing" functionality to define the walls of the vessel, AAA, etc. Post processing logic 540 may then accurately identify a size of the abdominal aorta and an AAA, if one exists. For example, post processing logic 540 may determine the largest diameter of the abdominal aorta, which may correspond to an AAA, as well as identify other parameters, such as length, cross-sectional area, etc. In this manner, the measurement of the abdominal aorta and a possible AAA will be more accurate as compared to using conventional 2D imaging.

In some implementations, such as when imaging a 3D tubular structure that is tortuous, determining the real diameter of the target organ/vessel using cross-sectional views may not be accurate. In such cases, post processing logic 540 may determine the diameter based on a 3D structure, as opposed to a 2D cross-sectional image. For example, image registration and stitching logic 530 and/or post processing logic 540 may register and/or combine multiple cross-sectional images in 3D space using information from the position sensors/encoders (e.g., position sensors 160 and/or encoders 190). In other instances, such as when images overlap, post processing logic 540 may use an image-based approach, such as cross-correlation to generate 3D image information, without relying on information from position sensors/encoders. In still other instances, image registration and stitching logic and/or post processing logic 540 may register and stitch together multiple 3D views. For example, two orthogonal arrays (e.g., transducers 222-1 and 224-1) can be used to generate a 3D volume image. In this case, image registration and stitching logic 530 may stitch together multiple 3D volume images. In each of these implementations which use 3D imaging, post processing logic 540 may determine the diameter based on generated 3D image information of the abdominal aorta.

In some implementations, post processing logic 540 may include machine learning/artificial intelligence logic to aid in identifying the abdominal aorta. For example, machine learning logic, such as convolutional neural networks, may be used to identify the abdominal aorta, as well as identify any overlying bowel gas. The machine learning logic may also aid in measuring the abdominal aorta diameter at multiple cross-sectional locations.

Display 550 may include an output device, such as a liquid crystal display (LCD), light emitting diode (LED) based display, etc., that displays images of the abdominal aorta and AAA, if one exists. In one implementation, display 550 may also display size information associated with the abdominal aorta, such as the diameter of the abdominal aorta.

The exemplary configuration illustrated in FIG. 5 is provided for simplicity. Controller 440 may include more or fewer logic units/devices than illustrated in FIG. 5. For example, controller 440 may include additional elements, such as communication interfaces (e.g., radio frequency transceivers) that transmit and receive information via external networks to aid in analyzing ultrasound signals to identify a target in a region of interest.

Figure 6:
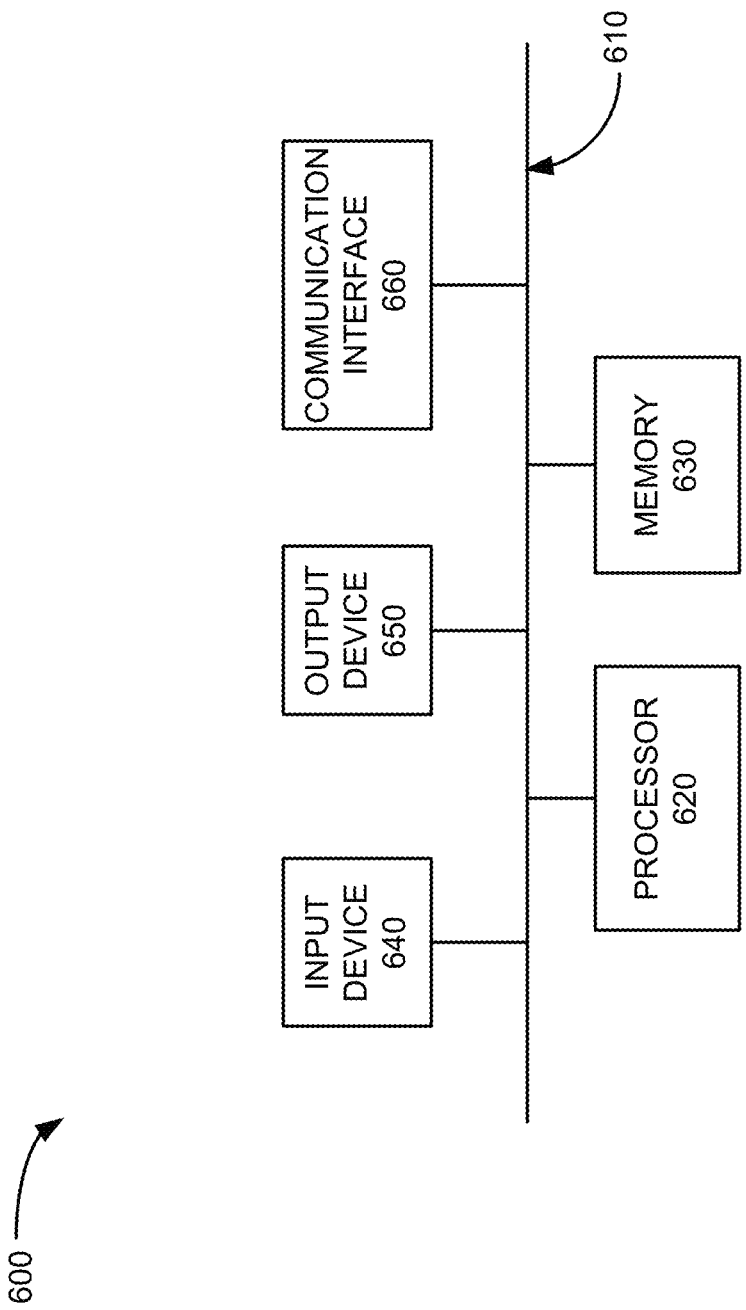
FIG. 6 illustrates an exemplary configuration of components included in one or more of the elements of FIGS. 1A-5.

FIG. 6 illustrates an exemplary configuration of a device 600 that may be used in accordance with an exemplary implementation. For example, device 600 may correspond to one or more components of CMUT systems 100, 140, 170 and/or 200, one or more components of probe 300 and/or one or more components of controller 440. As an example, components 400 in FIG. 4 and/or components of controller 440 illustrated in FIG. 5 may be implemented by device 600. Referring to FIG. 6, device 600 may include bus 610, processor 620, memory 630, input device 640, output device 650 and communication interface 660. Bus 610 may include a path that permits communication among the elements of device 600.

Processor 620 may include one or more processors, microprocessors, or processing logic that may interpret and execute instructions. Memory 630 may include a random access memory (RAM) or another type of dynamic storage device that may store information and instructions for execution by processor 620. Memory 630 may also include a read only memory (ROM) device or another type of static storage device that may store static information and instructions for use by processor 620. Memory 630 may further include a solid state drive (SDD). Memory 630 may also include a magnetic and/or optical recording medium (e.g., a hard disk) and its corresponding drive.

Input device 640 may include a mechanism that permits a user to input information to device 600, such as a keyboard, a keypad, a mouse, a pen, a microphone, a touch screen, voice recognition and/or biometric mechanisms, etc. Output device 650 may include a mechanism that outputs information to the user, including a display (e.g., a liquid crystal display (LCD)), a printer, a speaker, etc. In some implementations, a touch screen display may act as both an input device and an output device.

Communication interface 660 may include one or more transceivers that device 600 uses to communicate with other devices via wired, wireless or optical mechanisms. For example, communication interface 660 may include one or more radio frequency (RF) transmitters, receivers and/or transceivers and one or more antennas for transmitting and receiving RF data via a network. Communication interface 660 may also include a modem or an Ethernet interface to a LAN or other mechanisms for communicating with elements in a network.

The exemplary configuration illustrated in FIG. 6 is provided for simplicity. It should be understood that device 600 may include more or fewer devices than illustrated in FIG. 6. In an exemplary implementation, device 600 performs operations in response to processor 620 executing sequences of instructions contained in a computer-readable medium, such as memory 630. A computer-readable medium may be defined as a physical or logical memory device. The software instructions may be read into memory 630 from another computer-readable medium (e.g., a hard disk drive (HDD), SSD, etc.), or from another device via communication interface 660. Alternatively, hard-wired circuitry, such as application specific integrated circuits (ASICs), field programmable gate arrays (FPGAs), etc., may be used in place of or in combination with software instructions to implement processes consistent with the implementations described herein. Thus, implementations described herein are not limited to any specific combination of hardware circuitry and software.

Figure 7:
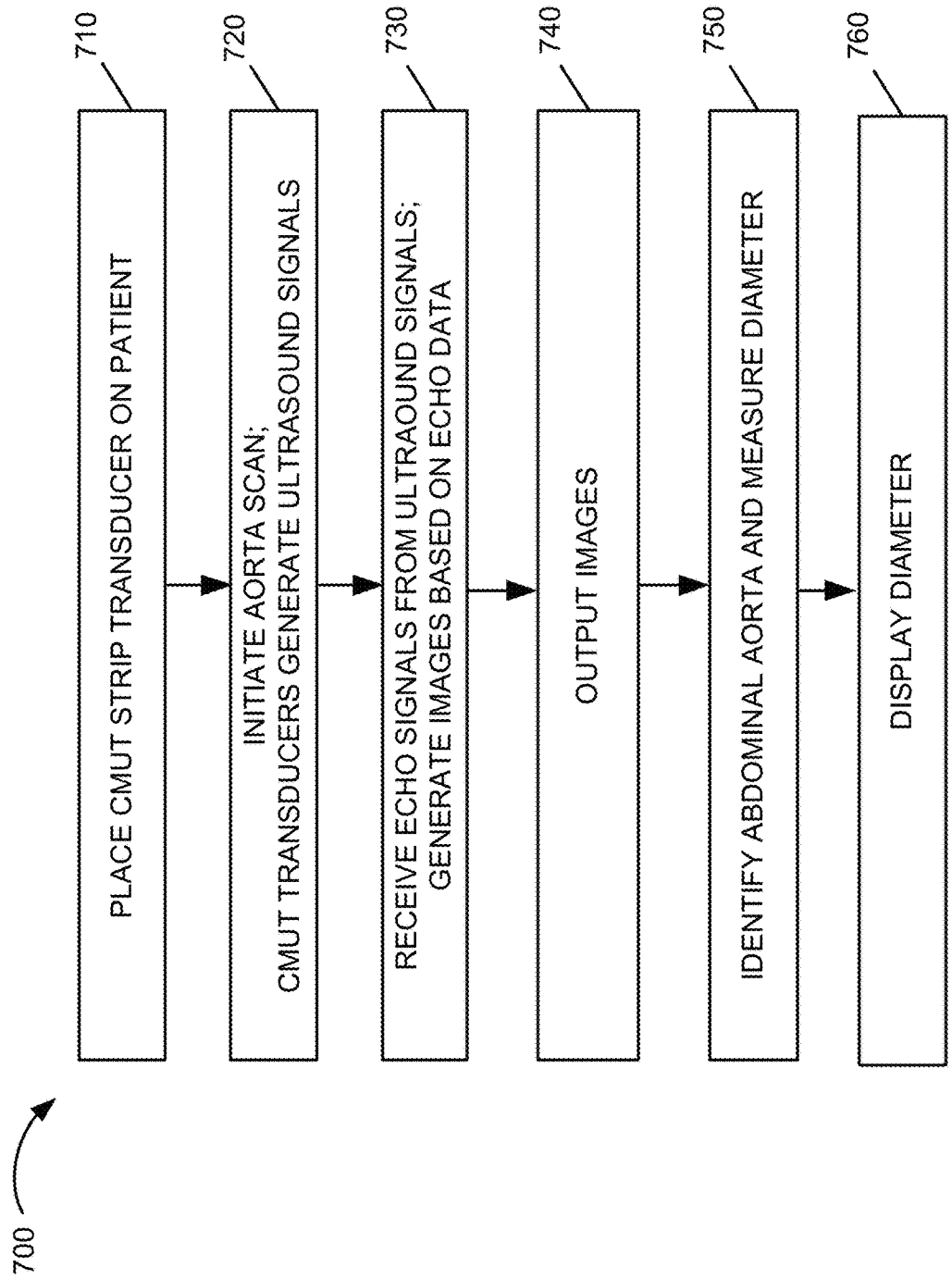
FIG. 7 is a flow diagram associated with scanning an abdominal aorta in accordance with an exemplary implementation.

FIG. 7 is a flow diagram illustrating exemplary processing 700 associated with performing an abdominal aorta scan, as well as identifying parameters associated with the abdominal aorta, such as identifying and measuring an AAA. In this example, the target for the ultrasound scan is the abdominal aorta. It should be understood, however, that features described herein may be used to identify other vessels, organs or structures within the body. Processing may begin with a user placing a CMUT system (e.g., CMUT system 100, 140, 170 or 200) on a patient (block 710). For example, referring to FIG. 8, medical personnel may place CMUT system 100 on the abdomen or abdominal wall overlying the abdominal aorta of patient 800. In some implementations, medical personnel may tape or otherwise adhere CMUT system 100 onto patient 800 to ensure that CMUT system 100 does not move or become dislodged during the scanning.

Figure 8:
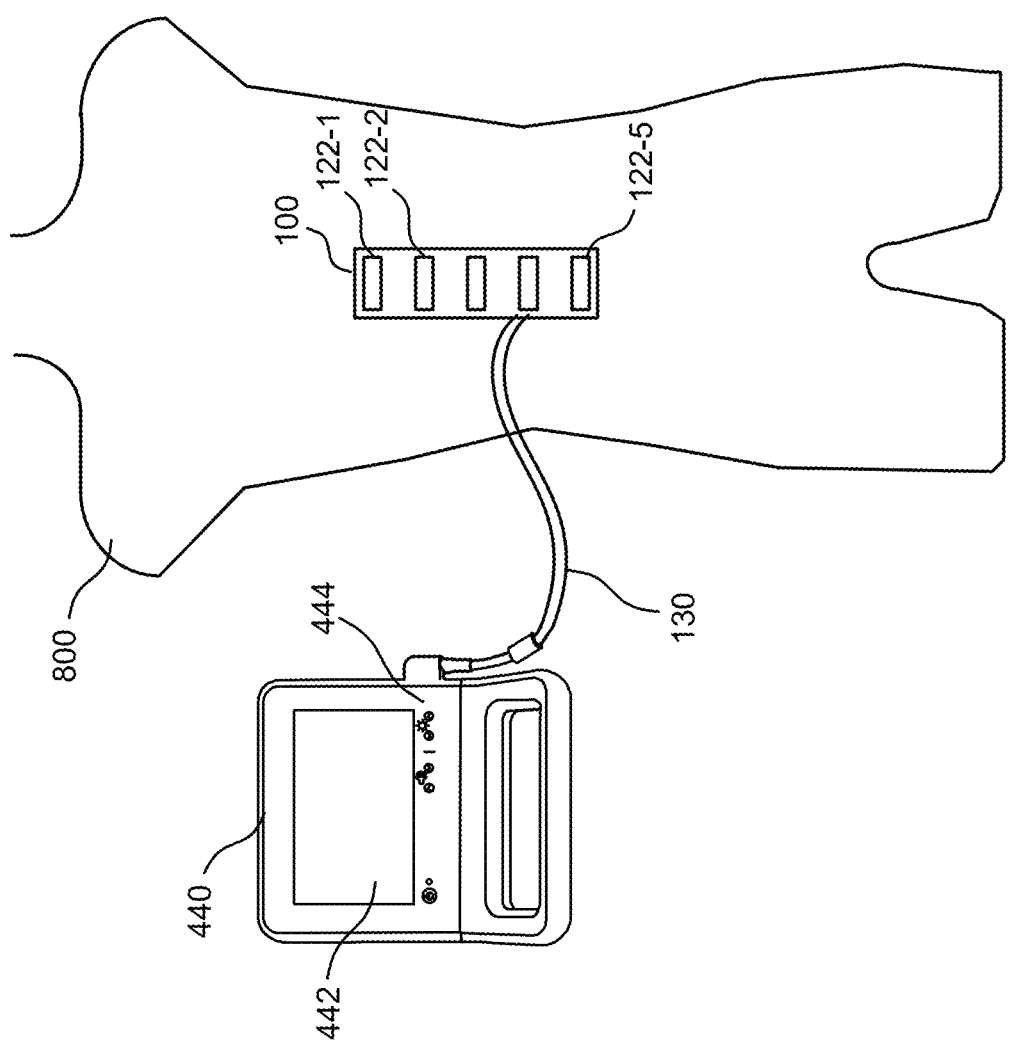
FIG. 8 illustrates an exemplary placement of the ultrasound transducer system of FIG. 1A on a patient in accordance with an exemplary implementation.

CMUT system 100 may be coupled to controller 440 via cable 130. In FIG. 8, controller 440 (also referred to as base unit 440) is a mobile computer device, similar in size to a laptop or tablet computer. In other implementations, controller 440 may be implemented via any relatively small computer device (e.g., similar in size to a smart phone) with a screen that is able to display ultrasound images.

In an exemplary implementation, a user may interact with controller 440 to initiate the ultrasound scan by, for example, selecting one or more inputs on display 442 or one or more buttons at area 444 (block 720). For example, controller 440 may include different buttons/selections that may be activated by touch on a graphical user interface (GUI) on display 442 or include one or more physical buttons at area 444 associated with different types of ultrasound scans, such as an aorta scan, an extremity/vein scan, a spinal scan, etc. In this example, assume that the medical personnel selects an abdominal aorta scan.

In response to receiving the selection to initiate the abdominal aorta scan, controller 440 may provide power/voltage to CMUT system 100. For example, controller 440 may provide voltage to CMUT system 100 via cable 130. AFE 410 of CMUT system 100 may then provide voltage/power to transducers 122 of CMUT system 100. For example, control logic in AFE 410 may sequentially provide voltage to each of CMUT transducers 122-1 through 122-5 illustrated in FIGS. 1A-1C. In response to the applied voltage, each transducer 122 may generate an ultrasound signal (block 720). The ultrasound signals may be transmitted through the abdominal wall of patient 800 and reach the target of interest (e.g., the abdominal aorta). The ultrasound signals may echo back from the abdominal aorta and body tissue to CMUT system 100. Data acquisition unit 430 receives the echo signals and may forward the echo signals to controller 440 (block 730).

Controller 440 may then generate images of the abdominal aorta based on the received echo signals (block 730). In an exemplary implementation, controller 440 may also receive position information with the received echo data. For example, as discussed above, CMUT system 100, 140, 170 and/or 200 may include position sensors 160 and/or position encoders 190 that provide position information associated with the transmitted ultrasound signals. For example, if power is provided to CMUT 122-1, position sensor 160 associated with CMUT 122-1 may provide the relative position information associated with CMUT 122-1. That is, images from a top portion of the abdominal aorta near the chest area, such as images from CMUT 122-1 may be rotated based on position information and/or combined with images from the upper abdominal area (e.g., from CMUTs 122-2 and 122-3) and lower abdominal area (e.g., from CMUTs 122-4 and 122-5) to create or stitch together images spanning the entire abdominal aorta. In this manner, when echo signals are received from CMUTs 122, the position information may be used to correlate the ultrasound image to the particular location on patient 800.

Figure 9A:
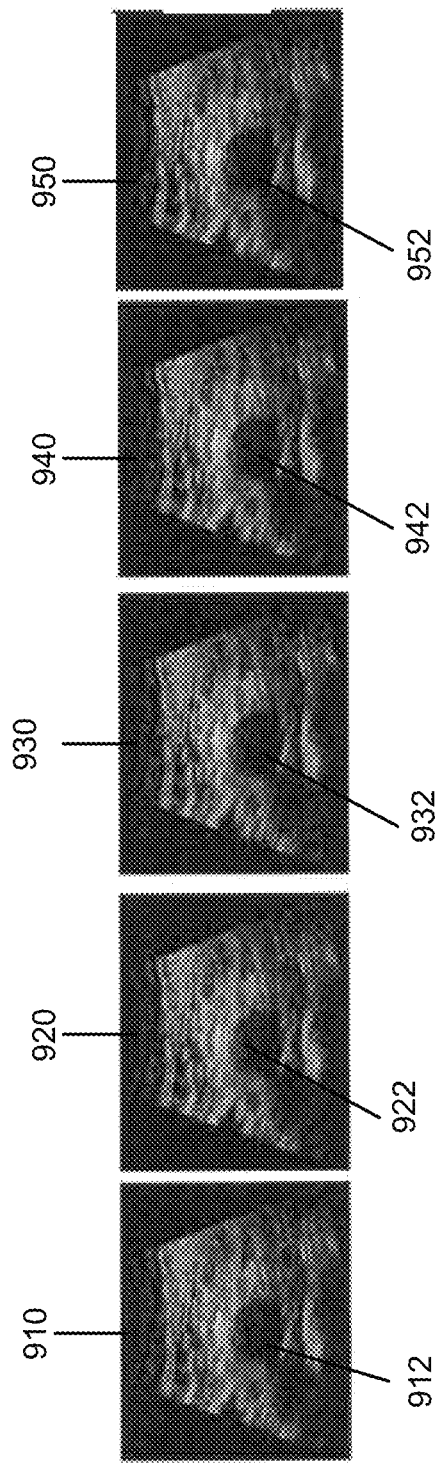
FIGS. 9A and 9B illustrate ultrasonic images generated in accordance with an exemplary implementation.

In each case, controller 440 may receive the echo data and position information and rotate and/or combine the image data to generate ultrasonic images of the abdominal aorta. In an exemplary implementation, controller 440 may output the images for display, such as on display 442 (block 740). For example, FIG. 9A illustrates exemplary images 910-950 of the abdominal aorta at each location associated with CMUTs 122-1 through 122-5, respectively. As illustrated, the abdominal aorta is labeled 912, 922, 932, 942 and 952, respectively. That is, vessel/organ identification unit 520 may identify an area of dark pixels as corresponding to the aorta or the lumen of the aorta.

Figure 9B:
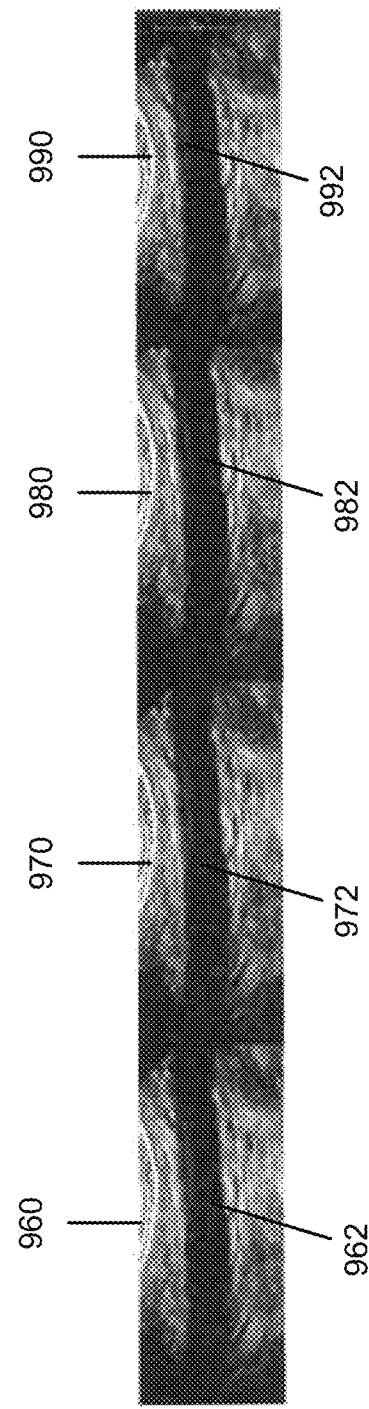

Image registration and stitching logic 530 may also register the multiple images and/or stitch or combine multiple images to display the length of the abdominal aorta, as illustrated in FIG. 9B. Referring to FIG. 9B, images 960-990 each illustrate an orthogonal view of the aorta, labeled 962, 972, 982 and 992, respectively.

Controller 440 may then measure the diameter of the abdominal aorta (block 750). For example, post processing logic 540 may measure the diameter of the abdominal aorta in each of images 910-950 and determine the largest value. Since an AAA may occur anywhere in the abdominal aorta, the largest diameter of the abdominal aorta may represent the most likely location of an AAA. Post processing logic 540 may output the diameter measurement to display 550 (block 760).

Figure 10:
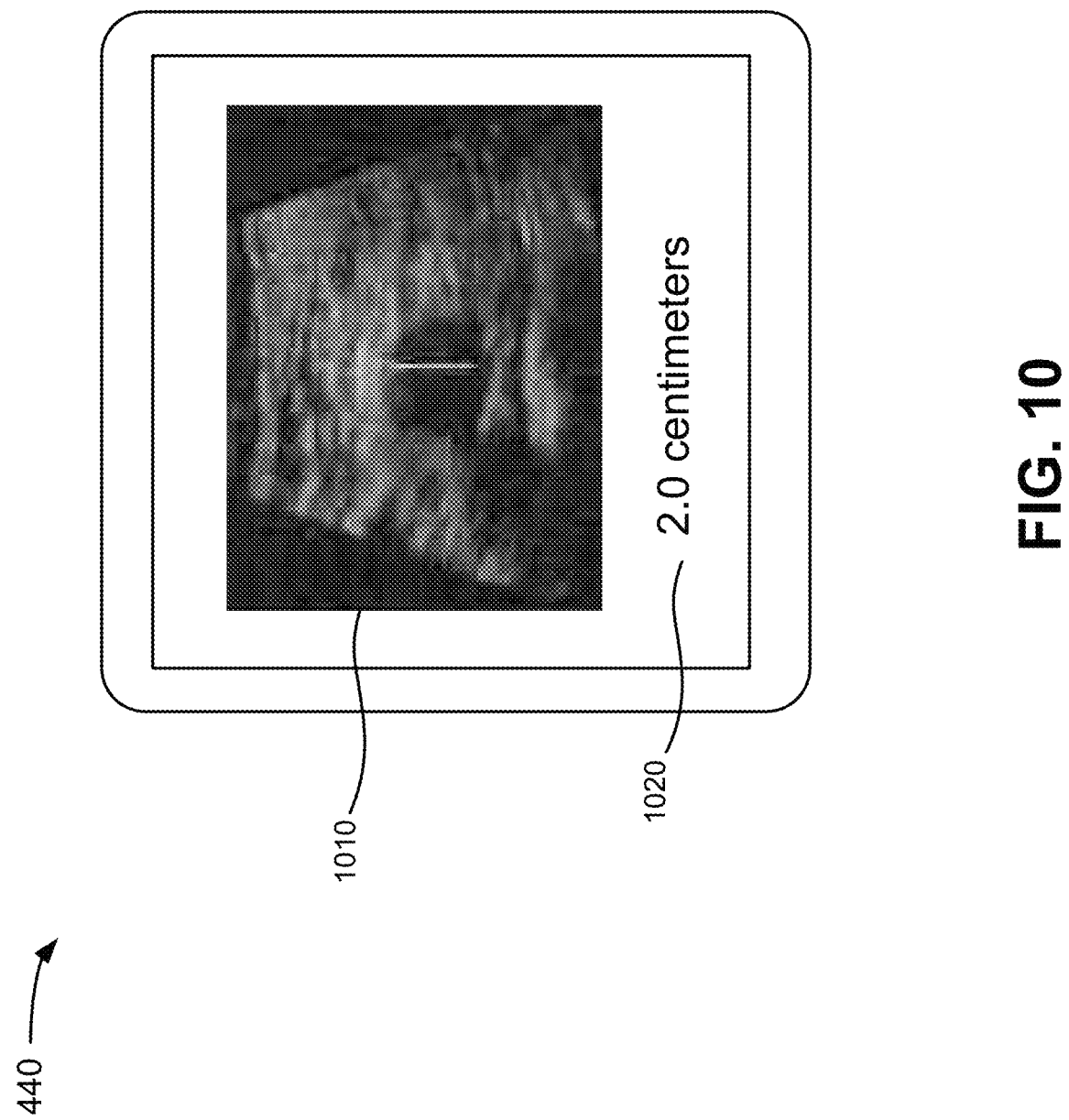
FIG. 10 illustrates an exemplary display associated with the processing of FIG. 7 in accordance with an exemplary implementation.

For example, referring to FIG. 10, controller 440 may display image 1010 of the abdominal aorta and display the text "2.0 centimeters" at area 1020. Medical personnel may then simply view controller 440 and determine that the maximum diameter of the abdominal aorta is less than the value typical of an AAA (e.g., 3.0 centimeters). In some implementations, controller 440 may also automatically determine the possibility of an AAA and optionally display information on controller 440 regarding the possibility. For example, if the largest maximum diameter is greater than 3.0 centimeters (e.g., 5.0 centimeters), controller 440 may output text or graphics indicating that an AAA may exist. In some implementations, post processing logic 540 may also output diameter information associated with the abdominal aorta at each location identified in images 910-960.

As described above, in some implementations, image registration and stitching logic 530 and/or post processing logic 540 may combine multiple 2D images to generate 3D images of the abdominal aorta. In such implementations, post processing logic 540 may determine the maximum diameter using the 3D images and output the diameter information at area 1020.

Figure 11A:
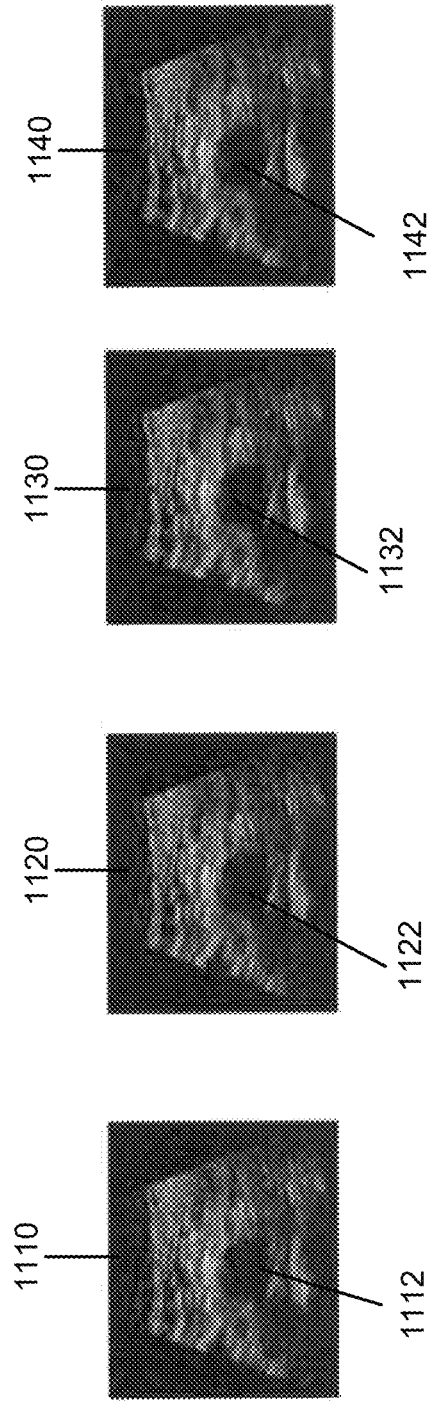
FIGS. 11A and 11B illustrate ultrasonic images generated in accordance with another exemplary implementation.

Referring back to FIG. 2, CMUT system 200, as described above, may include transducers 222 and 224 configured in pairs. Assuming that CMUT system 200 is being used, controller 400 may generate four images 1110 through 1140 illustrated in FIG. 11A. That is, image 1110 corresponds to the echo data associated with CMUTs 222-1 and 224-1, image 1120 corresponds to the echo data associated with CMUTs 222-2 and 224-2, etc. As illustrated, the abdominal aorta is labeled 1112, 1122, 1132 and 1142, respectively. That is, vessel/organ identification unit 520 may identify an area of dark pixels as corresponding to the abdominal aorta or the lumen of the abdominal aorta.

Figure 11B:
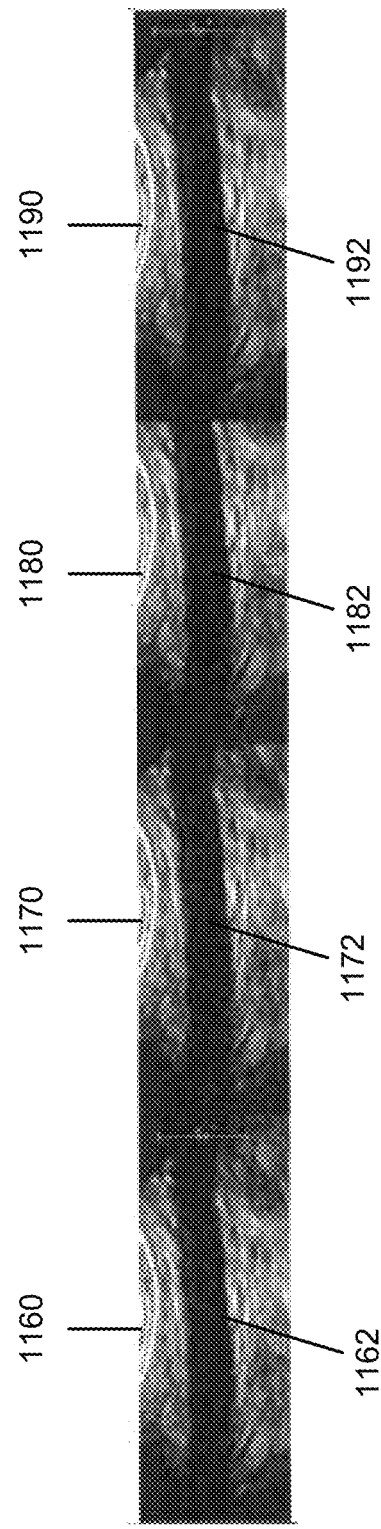

Image registration and stitching logic 530 may then register the multiple images and/or stitch or combine multiple images to display the length of the abdominal aorta, as illustrated in FIG. 11B. Referring to FIG. 11B, images 1160-1190 illustrate orthogonal views of the abdominal aorta, labeled 1162, 1172, 1182 and 1092, respectively. Similar to the discussion above with respect to FIGS. 7 and 10, controller 440 may output the image of the abdominal aorta on display 1010 and output the largest diameter or the diameter at each location of the abdominal aorta at area 1020. In this manner, medical personnel may be able to easily determine the maximum diameter of the abdominal aorta.

As also described above, in some implementations, image registration and stitching logic 530 and/or post processing logic 540 may combine multiple 2D images generated by CMUT system 200 to generate 3D images of the abdominal aorta. In such implementations, post processing logic 540 may determine the maximum diameter using the 3D images and output the diameter information at area 1020.

As described above, CMUT systems 100, 140, 170 and/or 200 may be used to generate ultrasound signals and receive echo signals from the ultrasound signals. As also described above, in another implementation, probe 300 may be used to generate ultrasound signals for imaging the abdominal aorta. In this implementation, probe 300 may not include base 310, theta motor 320 and dome 315, as illustrated in FIG. 12. A user (e.g., a medical technician, nurse, doctor, etc.) may move probe 300 along patient's 800 lower chest area to the abdomen (e.g., from the area above the xiphoid process to the umbilicus) to obtain images of the abdominal aorta. In this implementation, controller 440 may generate and display images of the abdominal aorta on display 1210 and also generate measurements of the abdominal aorta, such as the diameter. The maximum diameter of the abdominal aorta may be displayed at area 1220. In this implementation, medical personnel may move probe 300, and probe 300 provides wide fields of view that easily capture the entire abdominal aorta as the probe 300 is moved along patient 800's abdomen.

As described above, CMUT systems 100, 140, 170 and 200 may be used to generate imaging information, such as images of the abdominal aorta. For example, with respect to FIG. 1A, a one dimensional linear area of CMUTs 122 may be used to image a long, elongated structure, such as the abdominal aorta. In other implementations, other configurations of CMUTs, including 2D arrays, radial arrays, etc., may be used to image, for example, large three-dimensional volumes within the body. Still further, in some implementations, a "sparse" array of CMUTs may be used to image large 3D volumes efficiently, as described in detail below.

FIGS. 13A-13D illustrate top views of other CMUT systems that may be used in accordance with exemplary implementations. Referring to FIG. 13A, CMUT system 1310 includes an array of CMUTs 1312 (only one CMUT labeled for simplicity) similar to CMUT 100. In this implementation, CMUT system 1310 includes an array of 10 CMUTs. Such a configuration of CMUTs 1312 may be used to image an entire body cavity, such as from the neck to the groin area.

Referring to FIG. 13B, CMUT system 1320 also includes a 1D or 1.5D array of CMUTs 1322 oriented perpendicularly to CMUTs 1312. CMUT system 1320 may also be used to generate images that are included in a large portion of the body cavity. Referring to FIG. 13C, CMUT 1330 may include an array of CMUTs 1332 that are slightly offset from one another. This configuration of CMUTs 1332 may be useful in imaging a wider area within the body cavity than CMUT system 1310 or 1320. Referring to FIG. 13D, CMUT 1340 may include a two-dimensional (2D) array of CMUTs 1342 that are configured in two columns. Similar to CMUT system 1330, CMUT system 1340 may be useful when imaging a wide area within the body cavity.

FIGS. 14A-14C illustrate top views of still other CMUT systems 1410-1430. Referring to FIG. 14A, CMUT system 1410 includes an array of CMUTs 1412 (only one CMUT labeled for simplicity) arranged in two columns, with CMUTs 1412 in each column being configured perpendicularly to CMUTs 1412 in the adjacent column. Such a configuration of CMUTs 1412 may be used to image an entire body cavity.

Referring to FIG. 14B, CMUT system 1420 also includes a 1D array of CMUTs 1422. In this configuration, every other row includes one CMUT 1422 with the alternating row include two CMUTs 1422, with each row including CMUTs 1422 oriented perpendicularly to CMUTs in the adjacent row. CMUT system 1420 may also be used to generate images of a large portion of the body cavity. Referring to FIG. 14C, CMUT system 1430 may include an array of CMUTs 1432 that are grouped in rows with four CMUTs 1432. In this configuration, the two CMUTs 1432 located in the center of the four CMUTs 1432 are oriented perpendicularly to the two CMUTs located on the outside of the four CMUTs 1432. This configuration of CMUTs 1432 may be useful in imaging a wider area within the body cavity than CMUT system 1410 or 1420.

Figures 15A, 15B:
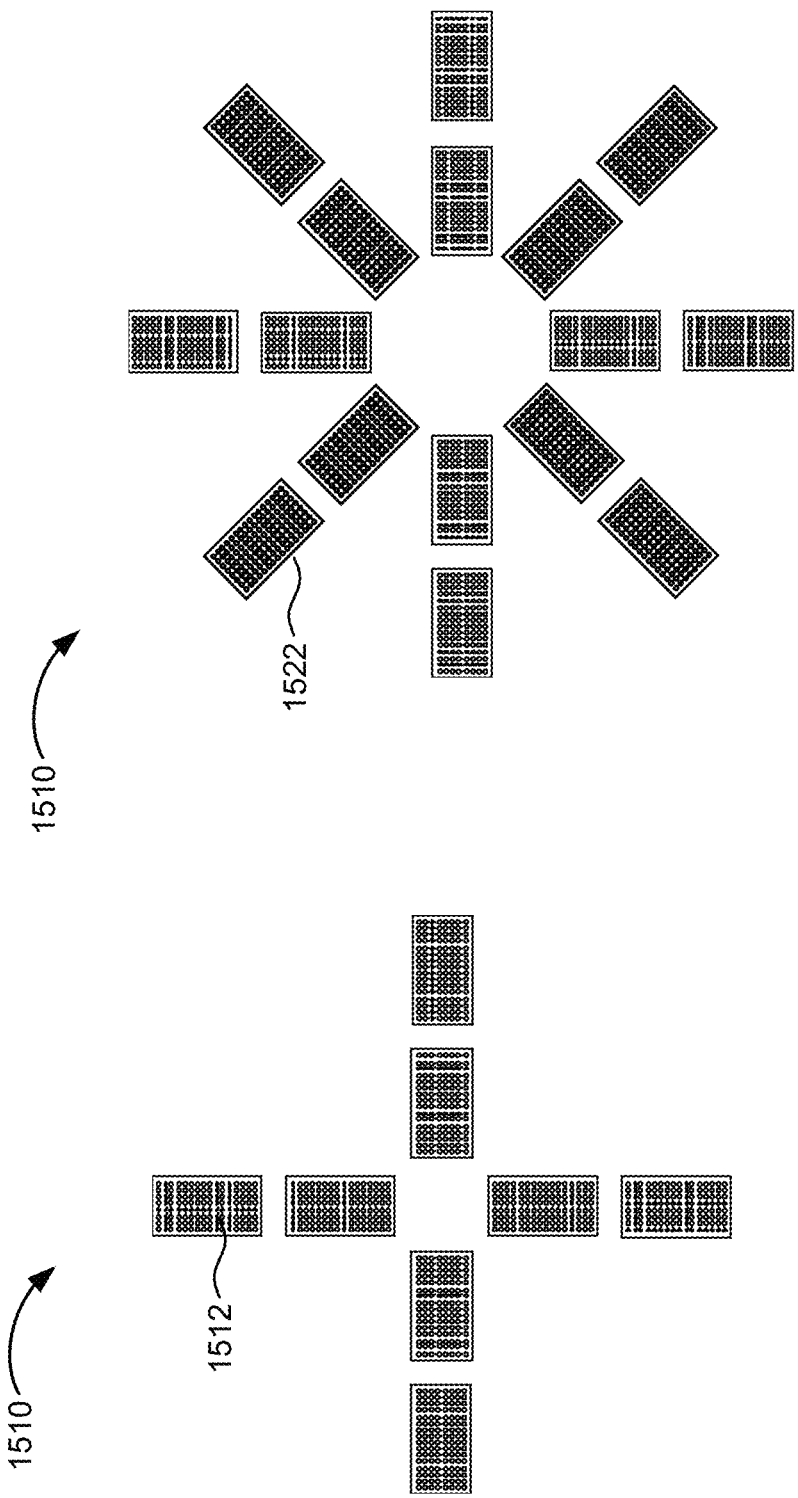
FIGS. 15A-15C are top views of other ultrasound transducer systems configured in radial patterns in accordance with other exemplary implementations.
Figure 15C:
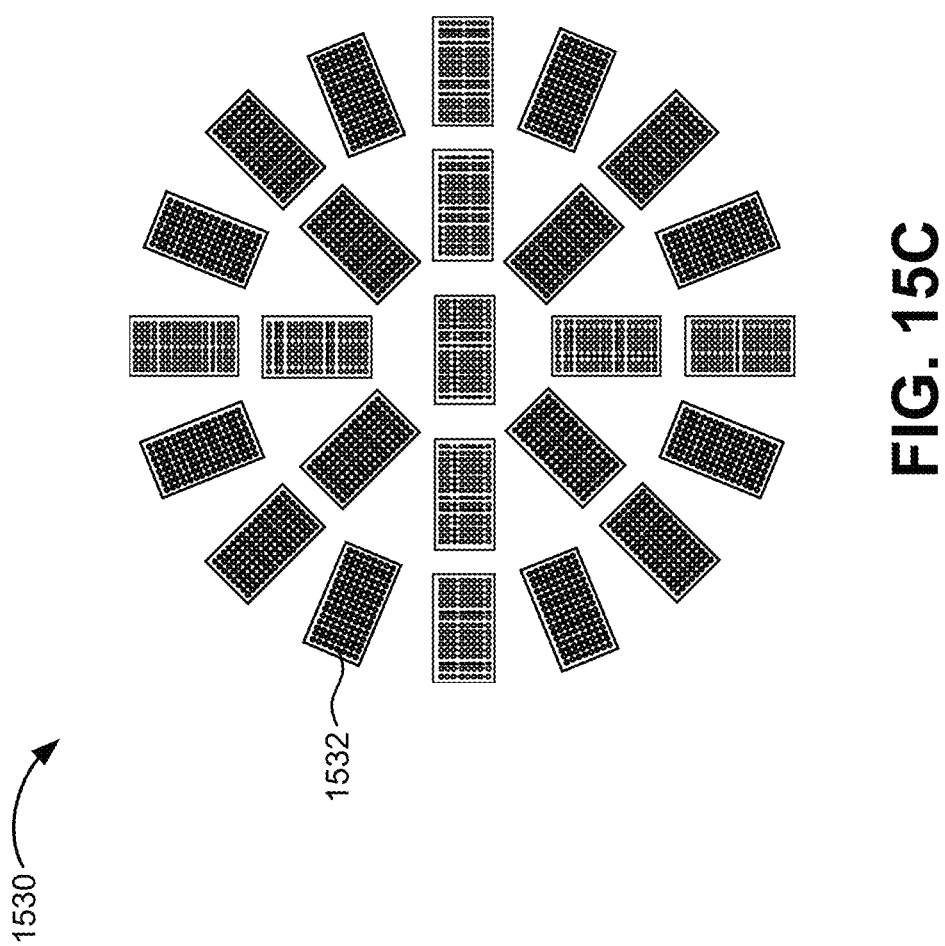

FIGS. 15A-15C illustrate top views of still other CMUT systems 1510-1530 that may be used in accordance with exemplary implementations. Referring to FIG. 15A, CMUT system 1510 includes a radial or cross pattern of CMUTs 1512 which extend outwardly from a center position. Such a configuration of CMUTs 1512 may be used to image a wide area of the body.

Referring to FIG. 15B, CMUT system 1520 also includes a radial pattern of CMUTs 1512 with eight lines of CMUTs 1522 extending radially from a center area. Again, this configuration of CMUTs 1522 may be used to image a wide area of the body. Referring to FIG. 15C, CMUT system 1530 may include an array of CMUTs 1532 in a radial pattern with 16 lines of CMUTs 1522 extending radially from a center area that also includes a CMUT 1532. This configuration of CMUTs 1532 may also be useful in imaging a wide area within the body cavity.

Figure 16D:
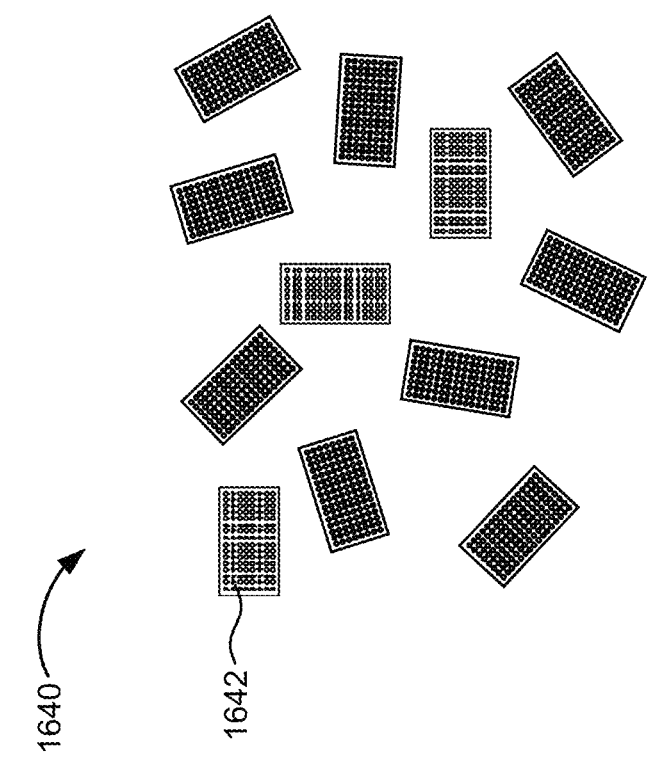

FIGS. 16A-16D illustrate top views of still other CMUT systems 1610-1640 that may be used in accordance with exemplary implementations. Referring to FIG. 16A, CMUT system 1610 includes a 2D array of CMUTs 1612 which include seven rows and five columns of CMUTs 1612. Such a configuration of CMUTs 1612 may be used to image a very wide area of the body.

Figure 16C:
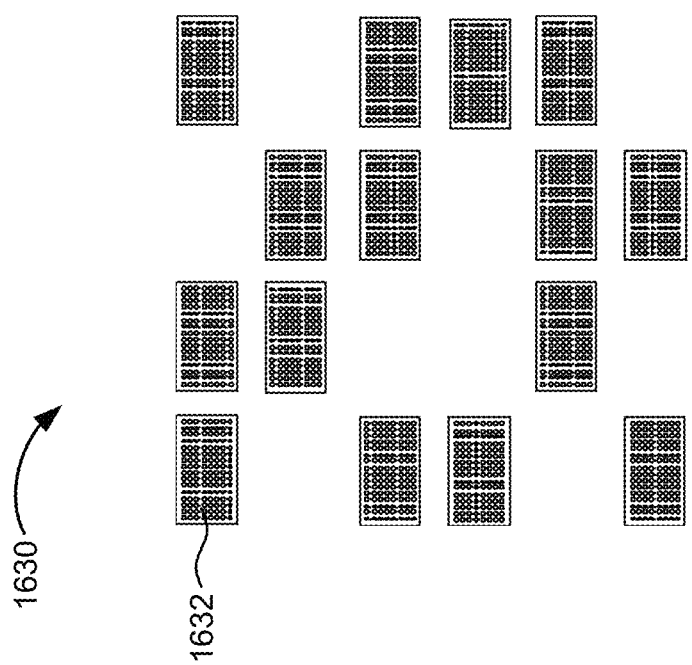

Referring to FIG. 16B, CMUT system 1620 also includes a 2D array of CMUTs 1622 that includes a number of rows and columns of CMUTs 1620 (e.g., six rows and five columns in this example, although other numbers of rows and columns of CMUTs 1620 may be used). The CMUTs 1622 in each column are oriented perpendicularly to adjacent CMUTs and perpendicularly to CMUTs 1622 in adjacent columns. Such a configuration may allow CMUT system 1620 to obtain a wider field of view than CMUT system 1610. Again, this configuration of CMUTs 1622 may be used to image a very wide area of the body. Referring to FIG. 16C, CMUT system 1630 includes a "sparse" array of CMUTs 1632 arranged in six rows and five columns. In this configuration, various rows and columns are not filled with CMUTs 1632, thereby reducing the overall number of CMUTs 1632 in CMUT system 1630. Such a configuration may reduce costs and/or processing time associated with generating images based on ultrasonic signals generated by CMUTs 1632 This configuration may also be useful in imaging large areas of the body cavity. Referring to FIG. 16D, CMUT system 1640 includes a "randomized" array of CMUTs 1640 in no particular/regular pattern. This configuration of CMUTs 1642 may also be useful in imaging a wide area within the body cavity.

Implementations described above provide for imaging the abdominal aorta. In some instances, bowel gas may cause problems associated with abdominal aorta imaging. For example, when bowel gas is present between the abdominal aorta and the transducer, a shadow caused by the bowel gas can block ultrasound signals from reaching the abdominal aorta and/or reflecting from the abdominal aorta. In some instances, an operator may provide pressure on the subject's abdomen to drive bowel gas from a current acoustic window. However, providing pressure may be uncomfortable for the patient/subject. In addition, attempting to move the bowel gas in this manner may be ineffective.

Figures 17A, 17B:
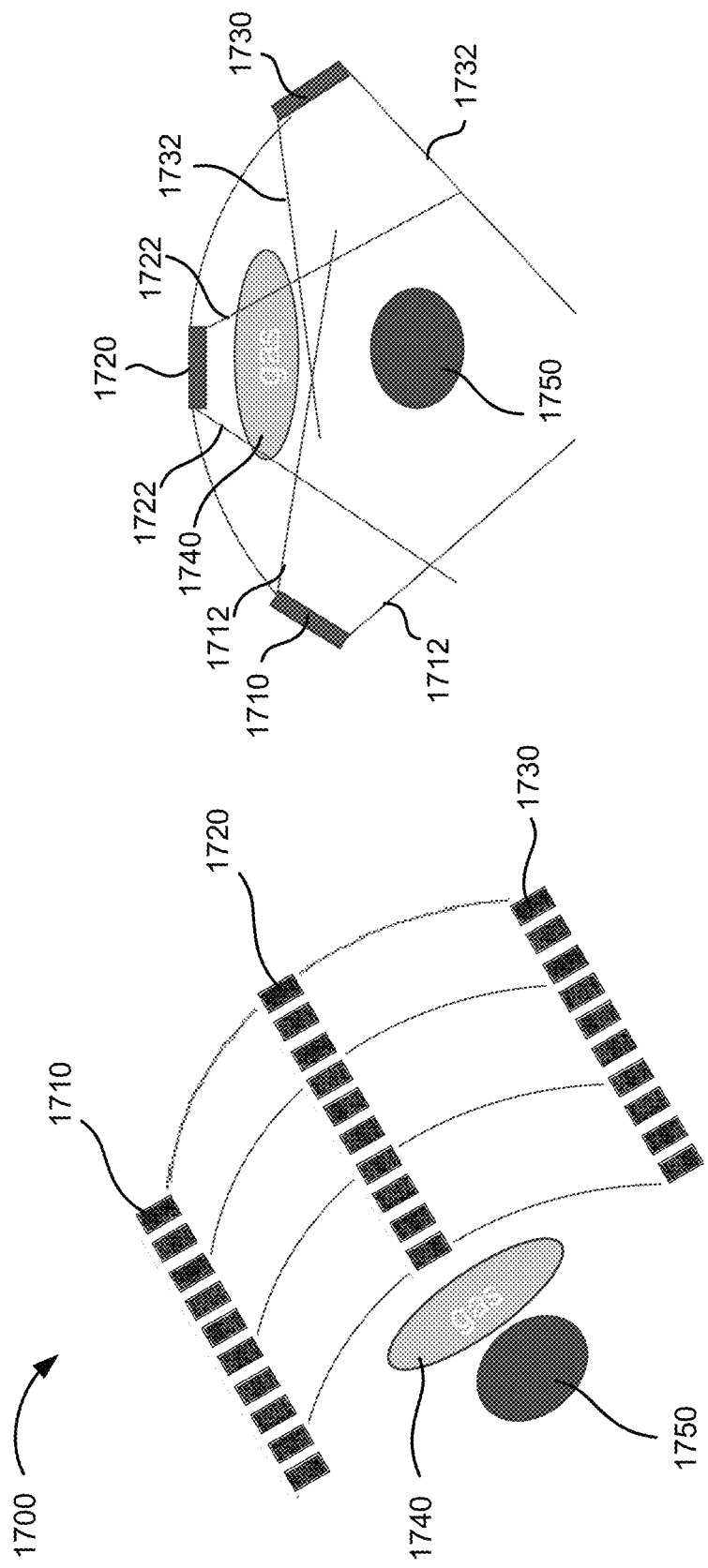
FIGS. 17A and 17B are views of another exemplary ultrasound transducer system used to mitigate the effects of bowel gas or other obstructions in accordance with an exemplary implementation.

In accordance with one exemplary implementation, multiple transducer strips may be used at different locations to mitigate problems associated with bowel gas. For example, FIG. 17A illustrates a transducer system 1700 that includes CMUT strips 1710, 1720 and 1730 and FIG. 17B illustrates fields of view associated with CMUT strips 1710, 1720 and 1730. As illustrated in FIG. 17A, CMUT strips 1710, 1720 and 1730 may each include a linear array of CMUT transducers similar to CMUT systems 100, 140 and 170 described above and illustrated in FIGS. 1A-1C. In CMUT system 1700, CMUT strip 1710 may be located to the left of CMUT strip 1720 and CMUT strip 1730 may be located to the right of CMUT strip 1720.

As illustrated in FIG. 17B, the field of view associated with the ultrasound signals from CMUT strip 1720 (represented by lines 1722) reaching the abdominal aorta, represented as element 1750, may be blocked by bowel gas, indicated as element 1740. However, in this implementation, CMUT strip 1710 may have a field of view (represented by lines 1712) that is not interfered with or blocked by bowel gas 1740. Similarly, CMUT strip 1730 may have a field of view (represented by lines 1732) that is not interfered with or blocked by bowel gas 1740. In this manner, CMUT system 1700 may capture images from the entire abdominal aorta 1750 which are not blocked by shadows associated with bowel gas 1740.

For example, similar to the discussion above with respect to position sensors 160 and/or encoders 190, each CMUT strip 1710-1730 may include similar position sensors/encoders. Image registration and stitching logic 530 may then register/rotate various B mode images obtained by CMUT strips 1710-1730 and/or stitch together the images to obtain images of the entire aorta not obstructed by bowel gas 1740 or other unwanted artifacts.

In addition, in this implementation, CMUT strips 1710-1730 are not fixed and may be moved. That is, strips 1710-1730 may be moved to capture images of the aorta through multiple acoustic windows at the same time. Using the overlapping or redundant configuration of CMUT strips 1710-1730 and the ability to physically move/relocate CMUT strips 1710-1730 on the surface of the patient's abdomen increases the likelihood that good quality images are obtained for the entire abdominal aorta even though unwanted image artifacts, such as bowel gas 1740 exist.

As described above, systems and methods described herein may use CMUT arrays and/or a curvilinear array of transducers to perform ultrasound imaging. In other implementations, an array of piezoelectric micro-machined ultrasonic transducers (PMUTs) may be used to generate ultrasonic images in a similar manner as the CMUT arrays described above.

In addition, features have been described above with respect to imaging an abdominal aorta. In other implementations, systems and methods described herein may be used to image other vessels, organ, body parts. For example, in another implementation, CMUT arrays (or PMUT arrays) may be used to image vessels, such as arteries and veins, in peripheral extremities, such as the arms or legs.

Figure 18:
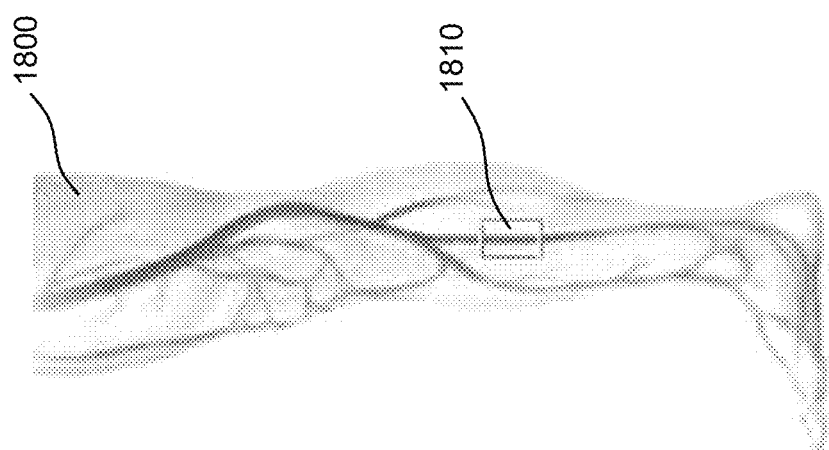
FIG. 18 illustrates another use of an ultrasound transducer system in accordance with another exemplary implementation.

For example, FIG. 18 illustrates an implementation in which a CMUT system 1810 is used to image a vein in the leg of patient 1800. In this implementation, CMUT system 1810 may include an array of CMUTs in any configuration described above. For example, in one implementation, CMUT system 1810 may be configured similar to CMUT system 140 and/or 170 described above. In this implementation, CMUT system 1810 may generate ultrasonic images of vein or artery in the lower leg. Similar imaging may be performed using CMUT arrays to image veins/arteries in a patient's arms.

Still further, CMUT arrays, PMUT arrays or a curvilinear arrays of transducers may be used to image a neonatal spine for neural tube defects or other anomalies. In each case, the size and configuration of transducers in the array may be based on the particular application. For example, for imaging a neonatal spine, a relatively small linear array of CMUTs may be used.

Implementations described herein have also been described as using a rigid or semi-rigid housing supporting CMUTs. In other implementations, the housing may be a continuous, flexible housing to house the CMUTs (or PMUTs). Using a flexible housing may aid in ensuring that the CMUTs system adheres to the skin of the patient.

In addition, features have been described above as using various types of position sensors to identify position or location information. In other implementations, other types of position sensors may be used. For example, electromagnetic position sensors may be used. In this implementation, an electromagnetic field generator may be used to generate an electromagnetic field. Based on the strength of the electromagnetic field, the electromagnetic position sensors located on the length of the housing (similar to position sensors 160) may determine their relative position. The electromagnetic position sensors may then provide position or location information to aid in combining ultrasonic images.

In still another implementation, optical markers may be used to generate position information. In this implementation, a camera-based optical tracker may be located over the patient and the camera may detect the optical markers to provide relative position information. The optical makers may be located on the length of the housing (similar to position sensors 160) and may be passive or active sensors. In each case, the optical markers and/or the camera-based optical tracker may provide position or location information to aid in combining ultrasonic images.

The foregoing description of exemplary implementations provides illustration and description, but is not intended to be exhaustive or to limit the embodiments to the precise form disclosed. Modifications and variations are possible in light of the above teachings or may be acquired from practice of the embodiments.

For example, features have been described above with respect to identifying a target of interest, such as a patient's abdominal aorta and an AAA, other vessels, such as veins or arteries in extremities and the neonatal spine. In other implementations, other vessels, organs or structures may be identified, and sizes or other parameters associated with the vessels, organs or structures may be estimated. For example, processing described herein may be used to perform prenatal ultrasound imaging, full abdominal imaging, full breast imaging, prostate imaging, thyroid imaging, kidney imaging, uterus imaging, ovaries imaging, heart imaging, etc.

Further, while series of acts have been described with respect to FIG. 7, the order of the acts may be different in other implementations. Moreover, non-dependent acts may be implemented in parallel.

It will be apparent that various features described above may be implemented in many different forms of software, firmware, and hardware in the implementations illustrated in the figures. The actual software code or specialized control hardware used to implement the various features is not limiting. Thus, the operation and behavior of the features were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as one or more processors, microprocessor, application specific integrated circuits, field programmable gate arrays or other processing logic, software, or a combination of hardware and software.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A system, comprising:
   a plurality of transducers located in a housing configured to be taped or adhered to a portion of a body or located on a flexible strip configured to be taped or adhered to the portion of the body, and configured to:
   transmit ultrasound signals directed to a target blood vessel, and
   receive echo information associated with the transmitted ultrasound signals;
   at least one processing device configured to:
   process the echo information and generate a plurality of ultrasound images of the target blood vessel,
   generate an estimated diameter of the target blood vessel at a plurality of locations based on the plurality of ultrasound images,
   output image information associated with the target blood vessel based on the plurality of ultrasound images, and
   output at least one of a maximum estimated diameter of the target blood vessel or the estimated diameters at the plurality of locations based on the image information; and
   a plurality of position sensors or encoders located in the housing or on the flexible strip, where each of the plurality of transducers is located adjacent one of the plurality of position sensors or encoders, and
   wherein when outputting image information associated with the target blood vessel, the at least one processing device is further configured to:
   determine a relative position associated with each of the plurality of ultrasound images based on data from the plurality of position sensors or encoders, and
   combine and rotate at least some of the plurality of ultrasound images to generate an image of the target blood vessel based on the determined relative position associated with each of the plurality of ultrasound images.

2. The system of claim 1, wherein the target blood vessel is an abdominal aorta and the plurality of ultrasound images comprise B-mode images or doppler generated images.

3. The system of claim 2, wherein the at least one processing device is further configured to:
   determine a possibility of an abdominal aortic aneurysm based on the maximum estimated diameter.

4. The system of claim 1, wherein the plurality of transducers comprise a plurality of capacitive micro-machined ultrasonic transducers (CMUTs).

5. The system of claim 4, wherein the plurality of transducers are located in the housing, and
   wherein the housing further comprises:
   a rigid, semi-rigid or flexible housing configured to house the plurality of CMUTs.

6. The system of claim 5, wherein the housing further comprises a plurality of portions, wherein at least some of the portions are configured to be angularly offset with respect to an adjacent one of the portions.

7. The system of claim 4, wherein the at least one processing device is located externally with respect to the housing, and wherein the housing includes a transmit device configured to forward echo information and position information to the at least one processing device.

8. The system of claim 1, further comprising:
   a display configured to:
   display the image information illustrating the blood vessel, and
   display information indicating the estimated maximum diameter of the blood vessel.

9. The system of claim 1, wherein the plurality of transducers comprise a plurality of piezoelectric micro-machined ultrasonic transducers (PMUTs).

10. The system of claim 1, wherein the plurality of transducers are located on a plurality of flexible strips, wherein each of the flexible strips is movable and is configured to be placed at a different location on a surface of the body.

11. The system of claim 1, wherein the plurality of transducers use at least one of pulsed wave or color doppler to generate the plurality of ultrasound images.

12. A method, comprising:
transmitting, via a plurality of ultrasound transducers located in a housing configured to be taped or adhered to a portion of a body or located on a flexible strip configured to be taped or adhered to a portion of the body, ultrasound signals directed to a target blood vessel;
receiving echo information associated with the transmitted ultrasound signals;
processing the echo information and generating a plurality of ultrasound images of the target blood vessel;
determining, using a plurality of position sensors located in the housing or on the flexible strip, relative position information associated with each of the plurality of ultrasound images, wherein each of the plurality of ultrasound transducers is located adjacent one of the plurality of position sensors;
combining at least some of the plurality of ultrasound images based on the relative position information to generate an image of the target blood vessel;
generating an estimated diameter of the target blood vessel at a plurality of locations based on the plurality of ultrasound images;
outputting the generated image of the target blood vessel; and
outputting at least one of a maximum estimated diameter of the target blood vessel or the estimated diameters at the plurality of locations based on the plurality of ultrasound images.

13. The method of claim 12, wherein the target blood vessel is an abdominal aorta and the plurality of ultrasound images comprise B-mode images or doppler generated images.

14. The method of claim 13, further comprising:
determining a possibility of an abdominal aortic aneurysm based on the maximum estimated diameter.

15. The method of claim 14, wherein the plurality of transducers comprises at least one of a plurality of capacitive micro-machined ultrasonic transducers (CMUTs), a plurality of piezoelectric micro-machined ultrasonic transducers (PMUTs) or a curvilinear array of transducers.

16. The method of claim 12, further comprising:
displaying the generated image illustrating the blood vessel; and
displaying information indicating the estimated maximum diameter of the blood vessel.

17. The method of claim 12, wherein the target blood vessel is a blood vessel in an arm or leg.

18. The method of claim 12, wherein the plurality of ultrasound transducers use at least one of pulsed wave or color doppler to generate the plurality of ultrasound images.

19. A non-transitory computer-readable medium having stored thereon sequences of instructions which, when executed by at least one processor, cause the at least one processor to:
transmit, via a plurality of ultrasound transducers located in a housing configured to be taped or adhered to a portion of a body or located on a flexible strip configured to be taped or adhered to a portion of the body, ultrasound signals directed to a target, wherein the target comprises a blood vessel or body part;
receive echo information associated with the transmitted ultrasound signals;
process the echo information and generate a plurality of ultrasound images of the target;
determine, using a plurality of position sensors located in the housing or on the flexible strip, relative position information associated with each of the plurality of ultrasound images, wherein each of the plurality of ultrasound transducers is located adjacent one of the plurality of position sensors;
combine and rotate at least some of the plurality of ultrasound images based on the relative position information to generate an image of the target;
generate an estimated parameter associated with the target at a plurality of locations based on the plurality of ultrasound images;
output the generated image of the target; and
output information associated with a potential defect in the target.

20. The non-transitory computer-readable medium of claim 19, wherein the target comprises an abdominal aorta, a blood vessel in an extremity or a spine and the plurality of ultrasound images comprise B-mode images or doppler generated images.

21. The non-transitory computer-readable medium of claim 19, wherein the target is an abdominal aorta, and the instructions further cause the at least one processor to:
generate a maximum estimated diameter of the abdominal aorta.

* * * * *